(12) United States Patent
Martin et al.

(10) Patent No.: US 11,274,273 B2
(45) Date of Patent: *Mar. 15, 2022

(54) MULTILAYERED CELL CULTURE APPARATUS

(71) Applicant: Corning Incorporated, Corning, NY (US)

(72) Inventors: Gregory Roger Martin, Acton, ME (US); Allison Jean Tanner, Portsmouth, NH (US)

(73) Assignee: Corning Incorporated, Corning, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/671,485

(22) Filed: Aug. 8, 2017

(65) Prior Publication Data

US 2017/0362554 A1 Dec. 21, 2017

Related U.S. Application Data

(60) Continuation of application No. 14/812,671, filed on Jul. 29, 2015, now Pat. No. 9,845,451, which is a
(Continued)

(51) Int. Cl.
*C12M 3/00* (2006.01)
*C12M 1/00* (2006.01)
(Continued)

(52) U.S. Cl.
CPC ............ *C12M 23/08* (2013.01); *C12M 23/04* (2013.01); *C12M 23/24* (2013.01); *C12M 23/34* (2013.01);
(Continued)

(58) Field of Classification Search
CPC ...... C12M 23/04; C12M 23/24; C12M 23/40; C12M 25/06
See application file for complete search history.

(56) References Cited

U.S. PATENT DOCUMENTS

| 3,459,176 A | 8/1969 | Leonard |
| 3,839,155 A | 10/1974 | McAleer et al. |

(Continued)

FOREIGN PATENT DOCUMENTS

| CA | 2105419 | 3/1994 |
| CN | 1441841 A | 9/2003 |

(Continued)

OTHER PUBLICATIONS

US 6,465,252 B1, 10/2002, Toner et al. (withdrawn)
(Continued)

*Primary Examiner* — Nathan A Bowers
(74) *Attorney, Agent, or Firm* — Troutman Pepper Hamilton Sanders LLP

(57) ABSTRACT

A multilayered cell culture apparatus for the culturing of cells is disclosed. The cell culture apparatus is defined as an integral structure having a plurality of cell culture chambers in combination with tracheal space(s). The body of the apparatus has imparted therein gas permeable membranes in combination with tracheal spaces that will allow the free flow of gases between the cell culture chambers and the external environment. The flask body also includes an aperture that will allow access to the cell growth chambers by means of a needle or cannula. The size of the apparatus, and location of an optional neck and cap section, allows for its manipulation by standard automated assay equipment, further making the apparatus ideal for high throughput applications.

10 Claims, 10 Drawing Sheets

Related U.S. Application Data continuation of application No. 14/699,157, filed on Apr. 29, 2015, now abandoned, which is a continuation of application No. 14/075,446, filed on Nov. 8, 2013, now Pat. No. 9,040,290, which is a continuation of application No. 13/904,171, filed on May 29, 2013, now Pat. No. 8,846,399, which is a continuation of application No. 13/591,566, filed on Aug. 22, 2012, now Pat. No. 8,470,589, which is a continuation of application No. 12/783,217, filed on May 19, 2010, now Pat. No. 8,273,572, which is a division of application No. 11/433,859, filed on May 11, 2006, now Pat. No. 7,745,209.

(60) Provisional application No. 60/702,896, filed on Jul. 26, 2005.

(51) Int. Cl.
  *C12M 1/24* (2006.01)
  *C12M 1/12* (2006.01)
  *C12M 1/04* (2006.01)
  *C12N 5/071* (2010.01)
  *C12M 1/34* (2006.01)

(52) U.S. Cl.
  CPC ............ *C12M 23/38* (2013.01); *C12M 23/58* (2013.01); *C12M 25/02* (2013.01); *C12M 25/04* (2013.01); *C12M 25/06* (2013.01); *C12M 29/04* (2013.01); *C12M 41/00* (2013.01); *C12N 5/0602* (2013.01)

(56) References Cited

U.S. PATENT DOCUMENTS

| | | |
|---|---|---|
| 3,853,712 A | 12/1974 | House et al. |
| 3,870,602 A | 3/1975 | Froman et al. |
| 3,873,423 A | 3/1975 | Munder et al. |
| 3,941,661 A | 3/1976 | Noteboom |
| 3,941,662 A | 3/1976 | Munder et al. |
| 3,948,732 A | 4/1976 | Haddad et al. |
| 4,142,940 A | 3/1979 | Modolell et al. |
| 4,225,671 A | 9/1980 | Puchinger et al. |
| 4,228,243 A | 10/1980 | Iizuka |
| 4,296,205 A | 10/1981 | Verma |
| 4,317,886 A | 3/1982 | Johnson et al. |
| 4,435,508 A | 3/1984 | Gabridge |
| 4,640,895 A | 2/1987 | Davis |
| 4,649,114 A | 3/1987 | Miltenburger et al. |
| 4,661,455 A | 4/1987 | Hubbard |
| 4,668,632 A | 5/1987 | Young et al. |
| 4,717,668 A | 1/1988 | Keilman et al. |
| 4,734,373 A | 3/1988 | Bartal |
| 4,748,124 A | 5/1988 | Vogler |
| 4,770,854 A | 9/1988 | Lyman |
| 4,824,787 A | 4/1989 | Serkes et al. |
| 4,829,002 A | 5/1989 | Pattillo et al. |
| 4,829,004 A | 5/1989 | Varani et al. |
| 4,839,292 A | 6/1989 | Cremonese |
| 4,847,462 A | 7/1989 | Soodak et al. |
| 4,897,359 A | 1/1990 | Oakley et al. |
| 4,906,577 A | 3/1990 | Armstrong et al. |
| 4,912,058 A | 3/1990 | Mussi et al. |
| 4,937,194 A | 6/1990 | Pattillo et al. |
| 4,937,196 A | 6/1990 | Wrasidlo et al. |
| 4,938,196 A | 7/1990 | Hoshi et al. |
| 4,939,151 A | 7/1990 | Bacehowski et al. |
| 4,945,203 A | 7/1990 | Soodak et al. |
| 4,960,706 A | 10/1990 | Bliem et al. |
| 5,017,490 A | 5/1991 | Taiariol et al. |
| 5,026,650 A | 6/1991 | Schwarz et al. |
| 5,047,347 A | 9/1991 | Cline |
| 5,068,195 A | 11/1991 | Howell et al. |
| 5,078,755 A | 1/1992 | Tozawa et al. |
| 5,079,168 A | 1/1992 | Amiot |
| 5,139,946 A | 8/1992 | Howell et al. |
| 5,139,951 A | 8/1992 | Butz et al. |
| 5,149,649 A | 9/1992 | Miyamori et al. |
| 5,153,131 A | 10/1992 | Wolf et al. |
| 5,173,225 A | 12/1992 | Range et al. |
| 5,225,346 A | 7/1993 | Matsumiya et al. |
| 5,240,854 A | 8/1993 | Berry et al. |
| 5,310,676 A | 5/1994 | Johansson et al. |
| 5,324,428 A | 6/1994 | Flaherty |
| 5,330,908 A | 7/1994 | Spaulding |
| 5,330,980 A | 7/1994 | Shin |
| 5,416,022 A | 5/1995 | Amiot |
| 5,426,037 A | 6/1995 | Pannell et al. |
| 5,437,998 A | 8/1995 | Schwarz et al. |
| 5,449,617 A | 9/1995 | Falkenberg et al. |
| 5,462,874 A | 10/1995 | Wolf et al. |
| 5,476,573 A | 12/1995 | Hirose et al. |
| 5,503,741 A | 4/1996 | Clark |
| 5,523,236 A | 6/1996 | Nuzzo |
| 5,527,705 A | 6/1996 | Mussi et al. |
| 5,565,353 A | 10/1996 | Klebe et al. |
| 5,576,211 A | 11/1996 | Falkenberg et al. |
| 5,589,112 A | 12/1996 | Spaulding |
| 5,597,731 A | 1/1997 | Young et al. |
| 5,602,028 A | 2/1997 | Minchinton |
| 5,627,070 A | 5/1997 | Gruenberg |
| 5,650,325 A | 7/1997 | Spielmann |
| 5,658,797 A | 8/1997 | Bader |
| 5,659,997 A | 8/1997 | Sprehe et al. |
| 5,670,332 A | 9/1997 | Kuhl et al. |
| 5,686,301 A | 11/1997 | Falkenberg et al. |
| 5,686,304 A | 11/1997 | Codner |
| 5,693,537 A | 12/1997 | Wilson et al. |
| 5,702,941 A | 12/1997 | Schwarz |
| 5,702,945 A | 12/1997 | Nagels et al. |
| 5,707,869 A | 1/1998 | Wolf et al. |
| 5,714,384 A | 2/1998 | Wilson et al. |
| 5,728,581 A | 3/1998 | Schwartz et al. |
| 5,736,398 A | 4/1998 | Giambernardi et al. |
| 5,759,847 A | 6/1998 | Eden et al. |
| 5,763,261 A | 6/1998 | Gruenberg |
| 5,763,267 A | 6/1998 | Kurjan et al. |
| 5,763,275 A | 6/1998 | Nagels et al. |
| 5,763,279 A | 6/1998 | Schwarz et al. |
| 5,783,075 A | 7/1998 | Eddleman et al. |
| 5,783,440 A | 7/1998 | Stevens |
| 5,786,215 A | 7/1998 | Brown et al. |
| 5,801,054 A | 9/1998 | Keil et al. |
| 5,866,400 A | 2/1999 | Palsson et al. |
| 5,866,419 A | 2/1999 | Meder |
| 5,876,604 A | 3/1999 | Nemser et al. |
| 5,902,747 A | 5/1999 | Nemser et al. |
| 5,912,177 A | 6/1999 | Turner et al. |
| 5,914,154 A | 6/1999 | Nemser |
| 5,924,583 A | 7/1999 | Stevens et al. |
| 5,928,936 A | 7/1999 | Ingram |
| 5,935,847 A | 8/1999 | Smith et al. |
| 5,985,653 A | 11/1999 | Armstrong et al. |
| 5,989,913 A | 11/1999 | Anderson et al. |
| 6,063,618 A | 5/2000 | Weuster-Botz et al. |
| 6,107,085 A | 8/2000 | Coughlin et al. |
| 6,114,165 A | 9/2000 | Cai et al. |
| 6,130,080 A | 10/2000 | Fuller |
| 6,150,159 A | 11/2000 | Fry |
| 6,190,913 B1 | 2/2001 | Singh |
| 6,228,607 B1 | 5/2001 | Kersten et al. |
| 6,297,046 B1 | 10/2001 | Smith et al. |
| 6,306,491 B1 | 10/2001 | Kram et al. |
| 6,323,022 B1 | 11/2001 | Chang et al. |
| 6,410,309 B1 | 6/2002 | Barbera-Guillem et al. |
| 6,455,310 B1 | 9/2002 | Barbera-Guillem |
| 6,465,243 B2 | 10/2002 | Okada et al. |
| 6,468,792 B1 | 10/2002 | Bader |
| 6,479,252 B1 | 11/2002 | Barbera-Guillem et al. |
| 6,518,035 B1 | 2/2003 | Ashby et al. |
| 6,548,263 B1 | 4/2003 | Kapur et al. |
| 6,555,365 B2 | 4/2003 | Barbera-Guillem et al. |
| 6,562,616 B1 | 5/2003 | Toner et al. |

(56) References Cited

U.S. PATENT DOCUMENTS

| | | |
|---|---|---|
| 6,569,672 B1 | 5/2003 | Laugham, Jr. et al. |
| 6,569,675 B2 | 5/2003 | Wall et al. |
| 6,576,458 B1 | 6/2003 | Sarem et al. |
| 6,588,586 B2 | 7/2003 | Abasolo et al. |
| 6,593,136 B1 | 7/2003 | Geiss |
| 6,605,463 B1 | 8/2003 | Bader |
| 6,653,124 B1 | 11/2003 | Freeman |
| 6,673,595 B2 | 1/2004 | Barbera-Guillem |
| 6,759,245 B1 | 7/2004 | Toner et al. |
| 6,794,184 B1 | 9/2004 | Mohr et al. |
| 6,811,752 B2 | 11/2004 | Barbera-Guillem |
| 6,818,438 B2 | 11/2004 | Muser |
| 6,821,772 B2 | 11/2004 | Barbera-Guillem et al. |
| 6,841,384 B2 | 1/2005 | Robbins, Jr. |
| 6,855,542 B2 | 2/2005 | DiMilla et al. |
| 6,881,752 B2 | 4/2005 | Vincent et al. |
| 6,900,055 B1 | 5/2005 | Fuller et al. |
| 6,908,767 B2 | 6/2005 | Bader |
| 7,022,518 B1 | 4/2006 | Feye |
| 7,078,228 B2 | 7/2006 | Lacey et al. |
| 7,160,687 B1 | 1/2007 | Kapur et al. |
| 7,192,769 B2 | 3/2007 | Pykett et al. |
| 7,195,758 B2 | 3/2007 | Schultze et al. |
| 7,195,785 B2 | 3/2007 | Babish et al. |
| 7,229,820 B2 | 6/2007 | Wilson |
| 7,560,274 B1 | 7/2009 | Fuller et al. |
| 7,745,209 B2 * | 6/2010 | Martin .................. C12M 23/04 435/294.1 |
| 8,158,426 B2 | 4/2012 | Wilson et al. |
| 8,158,427 B2 | 4/2012 | Wilson et al. |
| 8,168,432 B2 | 5/2012 | Wilson et al. |
| 8,178,345 B2 | 5/2012 | Bennett et al. |
| 8,216,828 B2 | 7/2012 | Cattadoris et al. |
| 8,273,572 B2 | 9/2012 | Martin et al. |
| 8,470,589 B2 * | 6/2013 | Martin .................. C12M 23/04 435/294.1 |
| 8,518,692 B2 | 8/2013 | Wilson |
| 8,697,443 B2 | 4/2014 | Wilson et al. |
| 8,809,044 B2 | 8/2014 | Wilson |
| 8,846,399 B2 | 9/2014 | Martin et al. |
| 8,927,267 B2 | 1/2015 | Bennett et al. |
| 9,040,290 B2 * | 5/2015 | Martin .................. C12M 23/04 435/294.1 |
| 9,045,721 B2 * | 6/2015 | Martin .................. C12M 23/04 |
| 9,290,730 B2 | 3/2016 | Martin et al. |
| 9,441,192 B2 | 9/2016 | Wilson et al. |
| 9,732,317 B2 | 8/2017 | Wilson |
| 9,845,451 B2 * | 12/2017 | Martin .................. C12M 23/04 |
| 10,144,910 B2 | 12/2018 | Tanner et al. |
| 2001/0055803 A1 | 12/2001 | Wall et al. |
| 2002/0039785 A1 | 4/2002 | Schroeder et al. |
| 2002/0110905 A1 | 8/2002 | Barbera-Guillem et al. |
| 2002/0119121 A1 | 8/2002 | Vitiello et al. |
| 2002/0197710 A1 | 12/2002 | Yoo et al. |
| 2003/0008388 A1 | 1/2003 | Barbera-Guillem et al. |
| 2003/0008389 A1 | 1/2003 | Carll |
| 2003/0017142 A1 * | 1/2003 | Toner .................. C12M 23/24 424/93.7 |
| 2003/0040104 A1 | 2/2003 | Barbera-Guillem |
| 2003/0077816 A1 | 4/2003 | Kronenthal et al. |
| 2003/0143727 A1 | 7/2003 | Chang |
| 2003/0157709 A1 | 8/2003 | DiMilla et al. |
| 2004/0007237 A1 | 1/2004 | Eubank |
| 2004/0029266 A1 | 2/2004 | Barbera-Guillem |
| 2004/0043481 A1 | 3/2004 | Wilson |
| 2004/0067585 A1 | 4/2004 | Wang et al. |
| 2004/0072347 A1 | 4/2004 | Schuler et al. |
| 2004/0110199 A1 | 6/2004 | Montemagno et al. |
| 2004/0132175 A1 | 7/2004 | Vetillard et al. |
| 2004/0259239 A1 | 12/2004 | Branson et al. |
| 2005/0009179 A1 | 1/2005 | Gemmiti et al. |
| 2005/0032205 A1 | 2/2005 | Smith et al. |
| 2005/0032208 A1 | 2/2005 | Oh et al. |
| 2005/0077225 A1 | 4/2005 | Usher et al. |
| 2005/0089993 A1 | 4/2005 | Boccazzi et al. |
| 2005/0101009 A1 | 5/2005 | Wilson et al. |
| 2005/0106717 A1 | 5/2005 | Wilson et al. |
| 2005/0169962 A1 | 8/2005 | Bhatia et al. |
| 2005/0260745 A1 | 11/2005 | Domansky et al. |
| 2006/0003436 A1 | 1/2006 | DiMilla et al. |
| 2006/0019361 A1 | 1/2006 | Ng et al. |
| 2006/0031955 A1 | 2/2006 | West et al. |
| 2006/0112438 A1 | 5/2006 | West et al. |
| 2006/0121606 A1 | 6/2006 | Ito et al. |
| 2006/0136182 A1 | 6/2006 | Vacanti et al. |
| 2006/0141617 A1 | 6/2006 | Desai et al. |
| 2006/0252150 A1 | 11/2006 | Cheng |
| 2006/0260745 A1 | 11/2006 | Tanaka et al. |
| 2007/0026516 A1 | 2/2007 | Martin et al. |
| 2008/0176318 A1 | 7/2008 | Wilson et al. |
| 2008/0206857 A1 | 8/2008 | Kenney et al. |
| 2008/0227176 A1 | 9/2008 | Wilson |
| 2015/0337252 A1 | 11/2015 | Martin et al. |
| 2021/0253997 A1 | 8/2021 | Wilson |

FOREIGN PATENT DOCUMENTS

| | | |
|---|---|---|
| DE | 4229334 | 3/1994 |
| EP | 0112155 A2 * | 6/1984 |
| EP | 0264464 | 4/1988 |
| EP | 0280054 A1 | 8/1988 |
| EP | 0307048 | 9/1988 |
| EP | 0155237 | 5/1989 |
| EP | 0337677 A2 * | 10/1989 |
| EP | 0353893 | 2/1990 |
| EP | 0647707 | 4/1995 |
| EP | 0700990 | 3/1996 |
| EP | 0725134 | 8/1996 |
| EP | 0866122 A2 | 9/1998 |
| EP | 0890636 | 10/2001 |
| EP | 1245670 | 10/2002 |
| EP | 2230297 A1 | 9/2010 |
| FR | 2666094 | 2/1992 |
| GB | 1539263 | 1/1979 |
| GB | 2268187 | 1/1994 |
| JP | 59-220182 | 12/1984 |
| JP | 62-228269 A | 10/1987 |
| JP | 64-034283 | 2/1989 |
| JP | 5-123182 | 5/1993 |
| JP | 7008267 | 1/1995 |
| JP | 734699 | 6/1995 |
| JP | 11028083 A | 2/1999 |
| JP | 2002528567 A | 9/2002 |
| JP | 2002-335946 | 11/2002 |
| JP | 2003-503022 | 1/2003 |
| JP | 2004129568 A | 4/2004 |
| JP | 2004-147555 | 5/2004 |
| JP | 2004-514432 A | 5/2004 |
| JP | 2004-535829 | 12/2004 |
| WO | 1989000188 | 1/1989 |
| WO | 90/05179 | 5/1990 |
| WO | 9013628 A1 | 11/1990 |
| WO | 91/15570 | 10/1991 |
| WO | 96/00780 | 1/1996 |
| WO | 96/00782 A1 | 1/1996 |
| WO | 1996/030497 | 10/1996 |
| WO | 98/17362 | 4/1998 |
| WO | 9831782 A1 | 7/1998 |
| WO | 98/53894 | 12/1998 |
| WO | 0024437 A2 | 5/2000 |
| WO | 00/56870 | 9/2000 |
| WO | 00/58437 | 10/2000 |
| WO | 00/78920 | 12/2000 |
| WO | 00/78932 | 12/2000 |
| WO | 01/92462 | 12/2001 |
| WO | 0204605 A2 | 1/2002 |
| WO | 2002/042419 A2 | 5/2002 |
| WO | 0242419 A3 | 5/2002 |
| WO | 02/064730 | 8/2002 |
| WO | 02/066595 | 8/2002 |
| WO | 2003/012081 A1 | 2/2003 |
| WO | 03/060061 | 7/2003 |
| WO | 03/085080 | 10/2003 |
| WO | 04/106484 | 12/2004 |

(56) References Cited

FOREIGN PATENT DOCUMENTS

| WO | 05/035728 | 4/2005 |
|---|---|---|
| WO | 0244341 A2 | 6/2006 |
| WO | 2007/015770 A1 | 2/2007 |

OTHER PUBLICATIONS

Barbera-Guillem "Overcoming Cell Culture Barriers to Meet the Demands of Cell Biology and Biotechnology," American Biotechnology Laboratory May 2001; 3 pages.
"Cell Culture Equipment (Hardware & Devices)", Lab Times, Products, Jan. 2006, pp. 52-58.
Derwent Abstract of EP0155236 Published Mar. 8, 1985.
Mamchaoui et al; "A Method for Measureing the Oxygen Consumption of Cell Monolayers," American Journal of Physiology. Lung Cellular and Molecular Physiology 278:L858-L863 (2000).
Metzen et al; "Pericellular PO2 and O2 Consumption in Monolayer Cell Cultures," Respiration Physiology; 100:101-106 (1995).
De Bartolo, L, et al., "A Novel Full-Scale Flat Membrane Bioreactor Utilizing Porcine Hepatocytes: Cell Viability and Tissue-Specific Functions", Biotechnol. Prog. 2000, 16, pp. 102-108.
PCT/US2006/027475 International Search Report dated Nov. 20, 2006.
PCT/US2006/027475 International Preliminary Report on Patentability dated Feb. 7, 2008.
Office Action dated Mar. 24, 2010, in Europe Patent Application No. 06787388.5.
Office Action dated Jan. 5, 2011, in Europe Patent Application No. 06787388.5.
Extended European Search Report dated Jun. 8, 2012, in Europe Patent Application No. 12163042.0.
Office Action dated Jun. 25, 2012, in Europe Patent Application No. 06787388.5.
Office Action dated Jan. 17, 2013, in Europe Patent Application No. 06787388.5.
File History for U.S. Pat. No. 8,809,044 issued Aug. 19, 2014.
Jensen, "Mass Cell Culture in a Controlled Environment," Cell Culture and Its Applications, Academic Press pp. 589-601 (1977).
Jensen, "Production of Anchorage-Dependent Cells—Problems and Their Possible Solutions," Biotechnology and Bioengineering Xxiii:2703-2716 (1981) (abstract only).
Vogler, "A Compartmentalized Device for the Culture of Animal Cells," Biomat. Art. Cells, Art. Org., 17(5):597-610 (1989).
Techno Plastics, Web Catalog (Jan. 2003) http://web.archive.org/web/20031209110901/http://www.ttp.ch/tis.
Mathiot et al., "Increase of Hybridoma Productivity Using an Original Dialysis Culture System," Cytotechnology 11:41-48 (1993) (abstract only).
Papas et al., "High-Density Culture of Human Islets on Top of Silicone Rubber Membranes," Transplantation Proceedings 37:3412-3414 (2005).
Written Opinion of the International Searching Authority for International Application No. PCT/US07/25110 (dated May 20, 2008).
Giarratana et al., "Cell Culture Bags Allow a Large Extent of Ex Vivo Expansion of LTC-IC and Functional Mature Cells Which Can Subsequently be Frozen: Interest for Large-Scale Clinical Applications," Bone Marrow Transplantation 22(7):707-715 (1998).
LifeCell® X-Fold™ Culture Bag commercial Product and Related Literature, © 2000.
Opticell® Commercial Product and Related Literature, © 2000.
OriGen PenmaLife™ Commercial Product and Related Literature at Least as of Sep. 17, 2004.
VectraCell™ Commercial Product and Related Literature, at Least as of Sep. 18, 2004.
VueLife™ Culture Bag Commercial Product and Related Literature, at Least as of Oct. 28, 2003.
PetriPERM Commercial Product and Related Literature, © 2003.
English Translation of Japanese Office Action (Notice of Reasons for Rejection) for Japanese Application No. 2006-534398 dated Nov. 9, 2010.
Nagel et al., "Membrane-Based Cell Culture Systems—an Alternative to in Vivo Production of Monoclonal Antibodies." Dev Biol Stand, 101:57-64 (1999) (abstract only).
Secker et al., "Gas-Permeable Lifecell Tissue Culture Flasks Give Improved Growth of Helicobacter Pylori in a Liquid Medium," J Clin Microbiol. 29(5):1060-1061 (1991).
Canadian Office Action for Canadian Application No. 2,671,812 dated Feb. 28, 2011.
Canadian Office Action for Canadian Application No. 2,671,967 dated Mar. 1, 2011.
European Search Report for European Application No. 11158157 dated Dec. 15, 2011.
EP Publication No. 1687400 published Aug. 9, 2006.
Publication re: VueLife™ Culture Bags Distributed by CellGeniz, available at least as early as Sep. 18, 2004. 5 pages.
Genetic Engineering News "OptiCell Concept for Cell Culture Operations," 20(21) Dec. 2000 (4 pages).
Budhiono et al., "Kinetic Aspects of Bacterial Cellulose Formation in nata-de-coco Culture System," Carbohydrate Polymers. 40:137-143 (1999).
Pulvertaft et al, "Activation of Lymphocytes," J. Clin. Path. 20:795-805 (1967).
Jensen et al., "Diffusion in Tissue Cultures on Gas-Permeable and Impermeable Supports," J. Theor. Biol. 56:443-458 (1976).
Kempner et al., "A Review of Cell Culture Automation", JALA vol. 7(2):56-62 (2002).
Kurosawa et al., "Primly Culture of Rat Hepatocytes on an Oxygen Permeable Membrane", Animal Cell Technology:Basic & Applied Aspects 12:91-95 (2002).
Answer filed Mar. 21, 2013 in *Wilson v. Corning, Inc.* in U.S. District Court for the District of Minnesota, Case No. 0:13-cv-00210-DWF-FLN.
Complaint filed Jan. 25, 2013 in *Wilson v. Corning, Inc.* in U.S. District Court for the District of Minnesota, Case No. 0:13-cv-00210-DWF-FLN.
Declaration of Interference filed Oct. 31, 2016 in Patent Interference No. 106,060.
Wilson List of Proposed Motions filed Dec. 8, 2016 in Patent Interference No. 106,060.
Martin Submission of Motions List filed Dec. 8, 2016 in Patent Interference No. 106,060.
Martin Substantive Motion 3 filed Feb. 15, 2017 for Patent Interference No. 106,060.
Second Declaration of Charles L. Crespi, Ph.D. dated Feb. 14, 2017 for Patent Interference No. 106,060.
Freshney, R.I., Culture of Animal Cells: A Manual of Basic Technique, 4th ed., pp. 24-27, 31-34, 89-104, 182 (Wiley-Blackwell 2000), Ex. 1013, Patent Interference No. 106,060.
Wilson Opposition 3, filed May 5, 2017, Patent Interference No. 106,060.
Declaration of John R. Wilson, dated May 5, 2017, Ex. 2004, Patent Interference No. 106,060.
Transcript of Cross Examination of Charles L. Crespi, Ph.D on Apr. 13, 2017, Ex. 2011, Patent Interference No. 106,060.
Martin Reply 3 (for unpatentability based on prior art), filed Jun. 14, 2017, Patent Interference No. 106,060.
Transcript of the Deposition of John R. Wilson taken May 31, 2017, Ex. 1055, Patent Interference No. 106,060.
Decision—Motions—Bd. R. 121(a), Dec. 26, 2017, Patent Interference No. 106,060.
Judgment—Bd. R. 127(a), Dec. 26, 2017, Patent Interference No. 106,060.
Wilson's Miscellaneous Motion 3 (request for rehearing of decision on motions and resulting judgment), filed Jan. 25, 2018, Patent Interference No. 106,060.
Martin Opposition 3 (for request for rehearing of decision on motions), filed Feb. 22, 2018, Patent Interference No. 106,060.
Decision on Rehearing—Bd. R. 125(c), Mar. 15, 2018, Patent Interference No. 106,060.

(56) References Cited

OTHER PUBLICATIONS

Brief of Appellant, John R. Wilson, filed Aug. 10, 2018, Appeal from the United States Patent and Trademark Office, Patent Trial and Appeal Board, in Interference No. 106,060, United States Court of Appeals for the Federal Circuit, Appeal No. 2018-1980.
BioCrystal Ltd., "Opticell TM—Building Block for Drug Discovery," Bioprocess Online, May 22, 2001.
Brief of Appellees, Gregory R. Martin and Allison J. Tanner, filed Sep. 19, 2018, Appeal from the United States Patent and Trademark Office, Patent Trial and Appeal Board, in Interference No. 106,060, United States Court of Appeals for the Federal Circuit, Appeal No. 2018-1980.
Reply Brief of Appellant, John R. Wilson, filed Oct. 17, 2018, Appeal from the United States Patent and Trademark Office, Patent Trial and Appeal Board, in Interference No. 106,060, United States Court of Appeals for the Federal Circuit, Appeal No. 2018-1980.
Judgment filed Oct. 21, 2019 in the U.S. Court of Appeals Court for the Federal Circuit, Case No. 18-1980 (ECF No. 51).
Opinion filed Oct. 21, 2019 in the U.S. Court of Appeals Court for the Federal Circuit, Case No. 18-1980 (ECF No. 50).
Request for Ex Parte Reexamination of U.S. Pat. No. 9,441,192 by Third-Party Requester Corning Incorporated filed Jun. 26, 2020.
Order Granting Request for Ex Parte Reexamination of U.S. Pat. No. 9,441,192 dated Jul. 31, 2020.
Patent Owner's Statement by Patent Owner Wilson Wolf Manufacturing Corporation filed Sep. 30, 2020 [filed in Reexam Control No. U.S. Appl. No. 90/014,540].
Reply of Third-Party Requester Corning Incorporated to Patent Owner's Statement under 35 U.S.C. 304 filed Nov. 30, 2020 [filed in Reexam Control No. U.S. Appl. No. 90/014,540].
Declaration of Charles L. Crespi, Ph.D. Pursuant to 37 C.F.R. 1.132 [filed in Reexam Control No. U.S. Appl. No. 90/014,540].
Complaint filed in *Wilson Wolf Mfg. Co.* v. *Brammer Bio, LLC*, Case No. 1:19-cv-02315-RGA (D. Del.).
First Amended Complaint filed in *Wilson Wolf Mfg. Corp.* v. *Sarepta Therapeutics, Inc.*, Case No. 1:19-cv-02316-RGA (D. Del.).
Complaint filed in *Wilson Wolf Mfg. Corp.* v. *Nationwide Children's Hosp., Inc et al.*, Case No. 2:20-cv-00192-MHW-CMV (S.D. Ohio).
Webster's Third New International Dictionary of the English Language, Unabridged, Merriam-Webster Inc., Springfield, MA (2002), pp. 66, 462, 1166.
Declaration of Charles L. Crespi, Ph.D. Pursuant to 37 C.F.R. 1.132 [filed in Reexam Control No. U.S. Appl. No. 90/014,541].
Dapstick, P.B., "Growth of Baby Hamster Kidney Cells in Suspension," Proc. R. Soc. Med. 56:1062-1064 (1963).
Dapstick et al., "Growth of a Cloned Strain of Hamster Kidney Cells in Suspended Cultures and their Susceptibility to the Virus of Foot-and-Mouth Disease," Nature 195:1163-1164 (1962) [filed in Reexam Control No. U.S. Appl. No. 90/014,540.
Reply Declaration of Charles L. Crespi, Ph D. Pursuant to 37 C.F.R. 1.132 [filed in Reexam Control Nos. U.S. Appl. No. 90/014,541 and U.S. Appl. No. 90/014,541].
Bognar et al., "Large Scale Propagation of BHK21 Cells Using the Opticell Culture System," J. Tissue Culture Methods 3(4):147-154 (1983).
Freshney, R. I., Culture of Animal Cells: A Manual of Basic Technique, 4th ed., (Wiley-Blackwell 2000), pp. 412-414.
Declaration of Dr. Maury D. Cosman [filed in Reexam Control Nos. U.S. Appl. No. 90/014,538, U.S. Appl. No. 90/014,538, and U.S. Appl. No. 90/014,538].
Declaration of Dr. Emilio Barbera-Guillem [filed in Reexam Control Nos. U.S. Appl. No. 90/014,538, U.S. Appl. No. 90/014,538, and U.S. Appl. No. 90/014,538].
Office Action dated Jun. 15, 2009 in U.S. Appl. No. 11/433,859.
Response of Oct. 14, 2009 in U.S. Appl. No. 11/433,859.
Response of Mar. 15, 2010 in U.S. Appl. No. 11/433,859.
Request for Ex Parte Reexamination of U.S. Pat. No. 8,697,443 by Third-Party Requester Corning Incorporated filed Jun. 26, 2020.
Order Granting Request for Ex Parte Reexamination of U.S. Pat. No. 8,697,443 dated Jul. 31, 2020.
Patent Owner's Statement by Patent Owner Wilson Wolf Manufacturing Corporation filed Sep. 30, 2020 [filed in Reexam Control No. U.S. Appl. No. 90/014,541].
Reply of Third-Party Requester Corning Incorporated to Patent Owner's Statement under 35 U.S.C. 304 filed Nov. 30, 2020 [filed in Reexam Control No. U.S. Appl. No. 90/014,541].
Ex Parte Reexamination Office Action dated Apr. 1, 2021 in Reexam Control No. U.S. Appl. No. 90/014,541.
Triaud et al., "Evaluation of Automated Cell Culture Incubators," J. Assoc. Lab. Auto. 8(6):82-86 (2003).
Request for Ex Parte Reexamination of U.S. Pat. No. 9,732,317 by Third-Party Requester Corning Incorporated filed Jun. 26, 2020.
Order Granting Request for Ex Parte Reexamination of U.S. Pat. No. 9,732,317 dated Aug. 4, 2020.
Patent Owner's Statement by Patent Owner Wilson Wolf Manufacturing Corporation filed Oct. 2, 2020 [filed in Reexam Control No. U.S. Appl. No. 90/014,538].
Reply of Third-Party Requester Corning Incorporated to Patent Owner's Statement under 35 U.S.C. 304 filed Dec. 2, 2020 [filed in Reexam Control No. U.S. Appl. No. 90/014,538].
Ex Parte Reexamination Office Action mailed Feb. 19, 2021 in Reexam Control No. U.S. Appl. No. 90/014,538.
Declaration of John Wilson dated Oct. 2, 2020 [filed in Reexam Control No. U.S. Appl. No. 90/014,538].
Corning Guide for Identifying and Correcting Common Cell Growth Problems (2008).
Titus et al., "Closed System Cell Culture Protocol Using HYPERStack Vessel with Gas Permeable Material Technology," J Vis. Exp. 45:e2499 (2010).
Declaration of Charles L. Crespi, Ph. D. Pursuant to 37 C.F.R. 1.132 [filed in Reexam Control No. U.S. Appl. No. 90/014,538].
Reply Declaration of Charles L. Crespi, Ph. D. Pursuant to 37 C.F.R. 1.132 [filed in Reexam Control No. U.S. Appl. No. 90/014,538.
Freshney, R.I., Culture of Animal Cells: A Manual of Basic Technique, 4th ed., (Wiley-Blackwell 2000), p. 77.
Webster's Third New International Dictionary of the English Language, Unabridged, Merriam-Webster Inc., Springfield, MA (2002), pp. 66, 1133, 1375-76, 1683, 1771, 2092.
Kurosawa et al., "Primary Culture of Rat Hepatocytes on an Oxygen Permeable Membrane," In: Animal Cell Technology: Basic & Applied Aspects, vol. 12, 91-95 (Shirahata S., Teruya K., Katakura Y. eds, 2002).
Civil Docket for Case No. 0:13-cv-00210-DWF-TNL in U.S. District Court for the District of Minnesota captioned *Wilson at al.* v *Corning, Inc.* as of May 17, 2021.
Joint Claim Construction Statement filed Dec. 9, 2013 (DI 83) in *Wilson* v. *Corning*, Case No. 0:13-cv-00210-DWF-TNL (D. Minn.).
Wilson Opening Claim Construction Memorandum filed Mar. 10, 2014 (DI 121) in *Wilson* v *Corning*, Case No. 0:13-cv-00210-DWF-TNL (D. Minn.).
Corning Responsive Claim Construction Brief filed Mar. 25, 2014 (DI 129) in *Wilson* v. *Corning*, Case No. 0:13-cv-00210-DWF-TNL (D. Minn.).
Wilson Responsive Claim Construction Brief filed Mar. 24, 2014 (DI 134) in *Wilson* v. *Corning*, Case No. 0:13-cv-00210-DWF-TNL (D. Minn.).
Corning Reply Claim Construction Brief filed Apr. 2, 2014 (DI 135) in *Wilson* v. *Corning*, Case No. 0:13-cv-00210-DWF-TNL (D. Minn.).
Wilson Reply Claim Construction Brief filed Apr. 2, 2014 (DI 136) in *Wilson* v. *Corning*, Case No. 0:13-cv-00210-DWF-TNL (D. Minn.).
Wilson Memorandum of Law in support of Motion to Voluntarily Dismiss Count VII Regarding Patent Infringement without Prejudice filed Jun. 23, 2014 (DI 179) in *Wilson* v. *Corning*, Case No. 0:13-cv-00210-DWF-TNL (D. Minn.).
Corning Memorandum in Response to Wilson Motion to Voluntarily Dismiss Regarding Patent Infringement Claims filed Jul. 14, 2014 (DI 206) in *Wilson* v. *Corning*, Case No. 0:13-cv-00210-DWF-TNL (D. Minn.).

(56) References Cited

OTHER PUBLICATIONS

Corning Memorandum in Support of Motion for Summary Judgment on Count VII of Plaintiffs' Complaint: Wilson's Patent Infringement Claims filed Jul. 14, 2014 (DI 209) in *Wilson v. Corning*, Case No. 0:13-cv-00210-DWF-TNL (D. Minn.).
Wilson Reply Memorandum in Support of Motion to Voluntarily Dismiss Count VII Regarding Patent Infringement Without Prejudice filed Jul. 18, 2014 (DI 220) in *Wilson v. Corning*, Case No. 0:13-cv-00210-DWF-TNL (D. Minn.).
Wilson Response Memorandum in Opposition to Corning Motion for Summary Judgment filed Under Seal Aug. 4, 2014 (DI 231) in *Wilson v. Corning*, Case No. 0:13-cv-00210-DWF-TNL (D. Minn.).
Corning Reply Memorandum in Support of Motion for Summary Judgment on Count VII of Plaintiffs' Complaint filed Aug. 18, 2014 (DI 237) in *Wilson v. Corning*, Case No. 0:13-cv-00210-DWF-TNL (D. Minn.).
Memorandum Opinion and Order regarding Claim Construction, Wilson Motion to Dismiss Count VII, and Coming Motion for Summary Judgment on Count VII of Plaintiffs' Complaint filed Mar. 17, 2015 (DI 299) in *Wilson v. Corning*, Case No. 0:13-cv-00210-DWF-TNL (D. Minn.).
Civil Docket for Case No. 0:20-cv-00700-DWF-TNL in U.S. District Court for the District of Minnesota captioned *Corning Incorporated v. Wilson Wolf Manufacturing Corporation et al.* as of May 17, 2021.
Complaint for Declaratory Judgment and Other Relief with Exhibits A-G filed Mar. 9, 2020 (DI 1) in *Corning v. Wilson*, Case No. 0:20-cv-00700-DWF-TNL (D. Minn.).
Wilson Answer to Complaint for Declaratory Judgment filed Oct. 20, 2020 (DI 46) in *Corning v. Wilson*, Case No. J:20-cv-00700-DWF-TNL (D. Minn.).
Amended Complaint for Declaratory Judgment and Other Relief with Exhibits A-M filed Feb. 19, 2021 (DI 73) in *Corning v. Wilson*, Case No. 0:20-cv-00700-DWF-TNL (D. Minn.).
Corning Prior Art Statement with Exhibits A-C dated Feb. 1, 2021 in *Corning v. Wilson*, Case No. 0:20-cv-00700-DWF-TNL (D. Minn.).
Wilson Claim Chart dated Feb. 1, 2021 in *Corning v. Wilson*, Case No. 0:20-cv-00700-DWF-TNL (D. Minn.).
Corning Prior Art Statement replacement pp. 443-445 served Feb. 3, 2021 in *Corning v. Wilson*, Case No. 0:20-cv-00700-DWF-TNL (D. Minn.).
Corning Non-Infringement Claim Charts with Exhibits A-D dated Mar. 15, 2021 (REDACTED) in *Corning v. Wilson*, Case No. 0:20-cv-00700-DWF-TNL (D. Minn.).
Wilson Responsive Prior Art Statement dated Mar. 15, 2021 in Corning v. Wilson, Case No. 0:20-cv-00700-DWF-TNL (D. Minn.).
Report on the Filing or Determination of an Action regarding a Patent, Mar. 11, 2013, 1 page, US Patent and Trademark Office.
Written Opinion from International Application No. PCT/US2009/049944 dated Jan. 8, 2010.
John R. Wilson and Wilson Wolf Manufacturing Corporation Memorandum Opinion and Order; United States District Court District of Minnesota, Case No. 0:13-cv-00210 (DI 388); filed Mar. 22, 2016; 26 pages.
Patent Owner's Response to Office Action, dated Apr. 19, 2021, Reexam Control No. U.S. Appl. No. 90/014,538.
Final Office Action dated Jun. 2, 2021, Reexam Control No. U.S. Appl. No. 90/014,538.
Second Declaration of Dr. Maury D. Cosman, dated Apr. 18, 2021, Exhibit 2016, Reexam Control No. U.S. Appl. No. 90/014,538.
Office Action dated Oct. 5, 2010 in U.S. Appl. No. 90/014,538, Exhibit 2017, Reexam Control No. U.S. Appl. No. 90/014,538.
Response to Restriction Requirement in U.S. Appl. No. 90/014,538, Exhibit 2018, Reexam Control No. U.S. Appl. No. 90/014,538.
Office Action dated Apr. 18, 2011 in U.S. Appl. No. 90/014,538, Exhibit 2019, Reexam Control No. U.S. Appl. No. 90/014,538.
Order of Oct. 6, 2020 in 0:20-cv-00700DWF-TNL, Exhibit 2020, Reexam Control No. U.S. Appl. No. 90/014,538.

Non Final Office Action dated Apr. 12, 2021, Reexam Control No. U.S. Appl. No. 90/014,540.
Request for Extension of Time dated Jun. 2, 2021, Reexam Control No. U.S. Appl. No. 90/014,540.
Non Final Office Action dated Apr. 1, 2021, Reexam Control No. U.S. Appl. No. 90/014,541.
Ex Parte Reexamination Interview Summary for Interview Dated May 27, 2021, dated Jun. 3, 2021 in Reexam Control No. U.S. Appl. No. 90/014,541.
Patent Owner's Response to Office Action, dated Jun. 1, 2021, Reexam Control No. U.S. Appl. No. 90/014,541.
Third Declaration of Dr. Maury D. Cosman, dated May 31, 2021, Exhibit 2021, Reexam Control No. U.S. Appl. No. 90/014,541.
Restriction Requirement dated Jun. 8, 2006 in U.S. Appl. No. 90/014,541, Exhibit 2022, Reexam Control No. U.S. Appl. No. 90/014,541.
CLINIcell® 250 Commercial Product and Related User Instructions V-2 (date unknown).
Corning Opening Claim Construction Brief filed Mar. 10, 2014 (DI 124) in *Wilson v. Corning*, Case No. 0:13-cv-00210-DWF (D. Minn.).
Application as Filed and File History Papers for U.S. Appl. No. 10/961,814 (Oct. 8, 2004 to Oct. 22, 2015).
Application as Filed and File History Papers for U.S. Appl. No. 11/505,122, now U.S. Pat. No. 3,415,144 (Aug. 16, 2006 to Mar. 3, 2015).
Application as Filed and File History Papers for U.S. Appl. No. 12/753,573, now U.S. Pat. No. 3,697,443 (Apr. 2, 2010 to Mar. 26, 2014).
Application as Filed and File History Papers for U.S. Appl. No. 11/952,856 (Dec. 7, 2007 to Mar. 5, 2013).
Application as Filed and File History Papers for U.S. Appl. No. 12/499,633, now U.S. Pat. No. 3,518,692 (Jul. 8, 2009 to Aug. 7, 2013).
Application as Filed and File History Papers for U.S. Appl. No. 13/029,762 now U.S. Pat. No. 3,168,432 (Feb. 17, 2011 to Apr. 11, 2012).
Application as Filed and File History Papers for U.S. Appl. No. 13/194,298, now U.S. Pat. No. 3,158,426 (Jul. 29, 2011 to Apr. 17, 2012).
Application as Filed and File History Papers for U.S. Appl. No. 13/194,363, now U.S. Pat. No. 3,158,427 (Jul. 29, 2011 to Nov. 19, 2013).
Defendants' Answer To Amended Complaint for Declaratory Judgment and Other Relief filed Oct. 2, 2021 (DI 129), in *Corning v. Wilson*, Case No. 0:20-cv-00700-DWF-TNL (D. Minn.).
Notice of Intent to Issue Ex Parte Reexamination Certificate, dated Oct. 15, 2021, in Reexamination Control No. U.S. Appl. No. 90/014,540.
Patent Owner's Response to Final Office Action, dated Oct. 19, 2021, in Reexamination Control No. U.S. Appl. No. 90/014,541.
Advisory Action, dated Aug. 19, 2021, Reexamination Control No. U.S. Appl. No. 90/014,538.
Patent Owner Response to Final Office Action, dated Aug. 2, 2021, Reexamination Control No. U.S. Appl. No. 90/014,538.
Applicant Summary of Interview, dated Jul. 28, 2021, Reexamination Control No. U.S. Appl. No. 90/014,540.
Patent Owner Response to Non-Final Office Action, dated Jul. 12, 2021, Reexamination Control No. U.S. Appl. No. 90/014,540.
Ex Parte Reexamination Interview Summary, dated Jun. 30, 2021, Reexamination Control No. U.S. Appl. No. 90/014,540.
Final Office Action, dated Jul. 19, 2021, Reexamination Control No. U.S. Appl. No. 90/014,541.
Memorandum Opinion and Order on Motion to Dismiss, Filed Sep. 17, 2021, in *Corning v. Wilson*, Case No. D:20-cv-00700-DWF-TNL (D. Minn.).
Corning Incorporated'S Responsive Claim Construction Brief filed Sep. 20, 2021 (DI 125), in *Corning v. Wilson*, Case No. 0:20-cv-00700-DWF-TNL (D. Minn.).
Defendants' Responsive Claim Construction Memorandum filed Sep. 20, 2021 (DI 121), in *Corning v. Wilson*, Case No. 0:20-cv-00700-DWF-TNL (D. Minn.).

(56) References Cited

OTHER PUBLICATIONS

Corning Cell CUBE® Systems URL:<https://ecatalog.corning.com/life-sciences/b2c/US/en/Bioprocess-and-Scale-up/CellCube%C2%AE/CellCube-System/Corning%C2%AE-CellCube%C2%AE-Systems/p/corningCellCubeSystems>, dated Mar. 1, 2021 (9 pages).

Corning Cell STACK® Culture Chambers URL:<https://ecatalog.corning.com/life-sciences/b2c/US/en/Browse-Products-by-Application/Cell-Therapy-and-Vaccines/CellSTACK%C2%AE/Corning%C2%AE-CellSTACK%C2%AE-Culture-Chambers/p/corningCellSTACKCultureChambers>, dated Mar. 1, 2021 (14 pages).

Corning E-CUBE™ Culture System Kit URL:<https://ecatalog.corning.com/life-sciences/b2c/US/en/Bioprocess-and-Scale-up/CellCube%C2%AE/E-Cube-System/E-Cube%E2%84%A2-Culture-System-Kit-%28without-CellCube%C2% AE-Module%29/p/3286>, dated Mar. 1, 2021 (6 pages).

Petaka™ Cell Culturing System URL: <https://www.neuromics.com/petaka-cell-culturingsystem>, dated Sep. 30, 2021 (3 pages).

Stang, B.V. "Monoclonal Antibody Production in Gas-Permeable Flexible Flasks, Using Serum-Free Media," Contemporary Topics, 37(6) 55-60 (1999).

Veliz, R.V. "Alternative Techniques to Obtain Monoclonal Antibodies at a Small Scale: Current State and Future Goals," Biotecnologia Aplicada, 19, 119-131 (2002).

U.S. Appl. No. 14/810,071, to John R. Wilson et al., filed Apr. 2, 2010, accessible to the USPTO via the electronic image file wrapper.

U.S. Appl. No. 60/509,651, to John R. Wilson et al., filed Oct. 8, 2003, accessible to the USPTO via the electronic image file wrapper.

U.S. Appl. No. 60/873,347, to John R. Wilson et al., filed Dec. 7, 2006, accessible to the USPTO via the electronic image file wrapper.

Defendants' Reply Claim Construction Memorandum, filed Oct. 26, 2021 (D1135), in *Corning v. Wilson*, Case No. 0:20-cv-00700-DWF-TNL (D. Minn.).

Corning Incorporated'S Reply Claim Construction Brief, filed Oct. 26, 2021 (D1137), in *Corning V. Wilson*, Case No. 0:20-cv-00700-DWF-TNL (D. Minn.).

Ex Parte Reexamination Advisory Action, Reexam Control No. U.S. Appl. No. 90/014,541, mailed Nov. 4, 2021.

Notice of Appeal, Reexamination Control No. U.S. Appl. No. 90/014,541, filed Dec. 17, 2021.

Appeal Brief, Reexamination Control No. U.S. Appl. No. 90/014,538, filed Dec. 1, 2021.

Second Request for Ex Parte Reexamination of U.S. Pat. No. 9,441,192 by Corning Incorporated, Reexamination Control No. U.S. Appl. No. 90/019,042, filed Dec. 8, 2021.

Declaration of Charles L. Crespi, Ph.D., Pursuant to 37 C.F.R. 1.132, Ex 1002 to Second Request for Ex Parte Reexamination of U.S. Pat. No. 9,441,192, Reexamination Control No. U.S. Appl. No. 90/019,042, dated Dec. 8, 2021.

Order Granting Ex Parte Reexamination of U.S. Pat. No. 9,441,192, Reexamination Control No. U.S. Appl. No. 90/019,042, dated Jan. 14, 2022.

\* cited by examiner

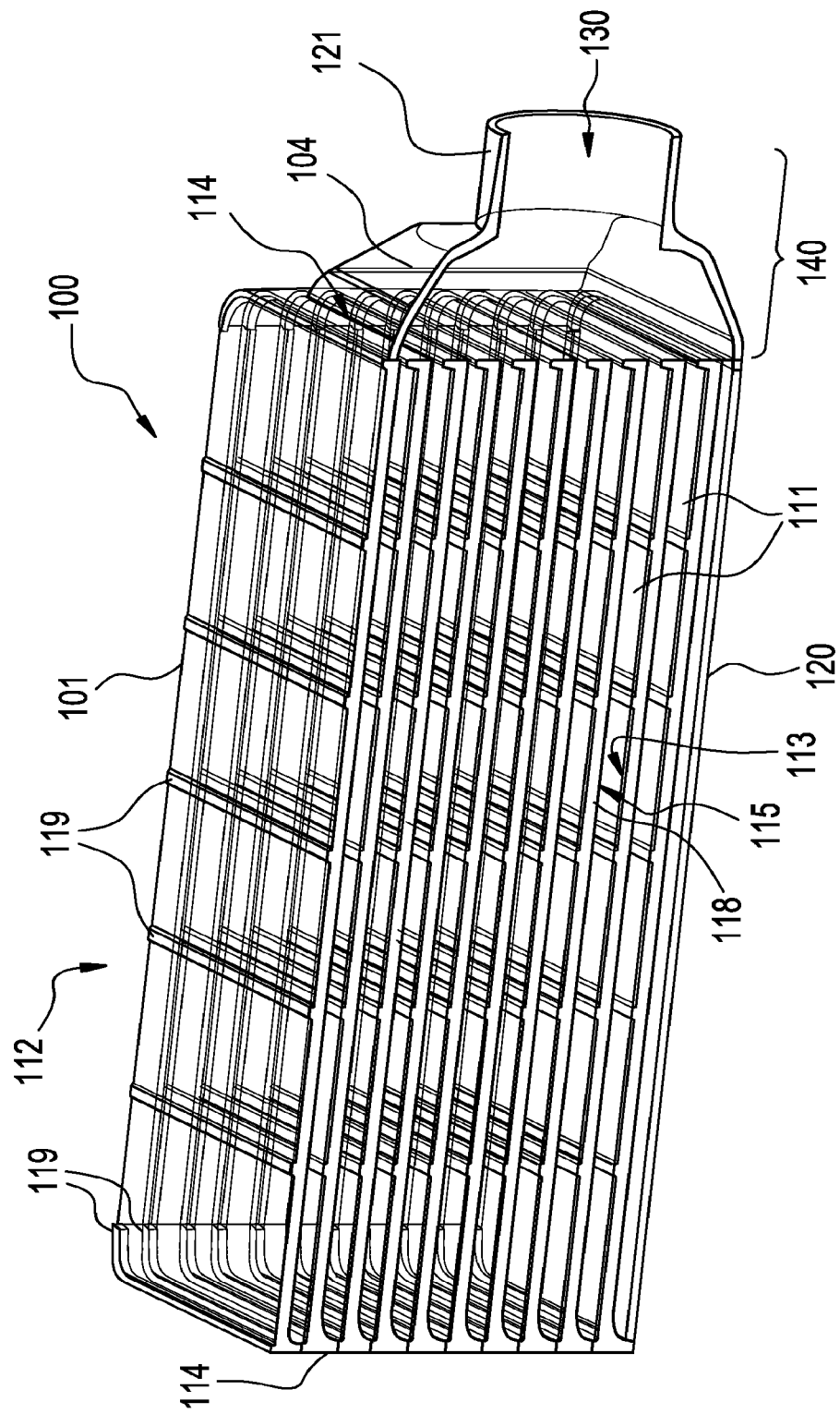

MULTILAYERED CELL CULTURE APPARATUS

CROSS-REFERENCE TO RELATED APPLICATIONS

This application is a continuation of U.S. patent application Ser. No. 14/812,671, filed on Jul. 29, 2015, which is a continuation of U.S. application Ser. No. 14/699,157, filed on Apr. 29, 2015, which is a continuation of U.S. application Ser. No. 14/075,446, filed on Nov. 8, 2013, which is a continuation of U.S. application Ser. No. 13/904,171, filed on May 29, 2013, which is a continuation of U.S. application Ser. No. 13/591,566, filed on Aug. 22, 2012, which is a continuation of U.S. application Ser. No. 12/783,217, filed on May 19, 2010, which is a divisional of U.S. application Ser. No. 11/433,859, filed on May 11, 2006, which claims the benefit of priority to U.S. Provisional Application Ser. No. 60/702,896 filed on Jul. 26, 2005, and entitled "Multilayered Cell Culture Apparatus" which is incorporated by reference herein.

FIELD OF THE INVENTION

The present invention relates generally to the cellular biological field and, in particular, to a cell cultivating flask.

BACKGROUND OF THE INVENTION

In vitro culturing of cells provides material necessary for research in pharmacology, physiology, and toxicology. The environmental conditions created for cultured cells should resemble as closely as possible the conditions experienced by the cells in vivo. One example of a suitable environment for culturing cells is a common laboratory flask such as demonstrated in U.S. Pat. No. 4,770,854 to Lyman. The cells attach to and grow on the bottom wall of the flask, immersed in a suitable sustaining media. The flask is kept in an incubator to maintain it at the proper temperature and atmosphere.

Although most cells will tolerate a hydrogen ion concentration (pH) range of 6.8 to 7.8, the optimal pH for growth of mammalian cells is 7.2 to 7.4. For the optimal pH to be maintained during cell cultivation, the cell culture medium must contain a buffering system. Frequently, pH is maintained by using a bicarbonate buffering system in the medium, in conjunction with an incubator atmosphere of approximately 5 to 7 percent carbon dioxide by volume. The carbon dioxide reacts with the water to form carbonic acid which in turn interacts with bicarbonate ions in the medium to form a buffering system which maintains the pH near physiological levels. Entry of carbon dioxide from the incubator into the cell culture flask is generally achieved by using a loosely fitting or vented cap or cover so that the small opening remains for the exchange of gas between flask and incubator. Further, flasks have been sold that are made from impact resistant polystyrene plastic which is permeable to water vapor, oxygen and carbon dioxide. However, relying only on the gas exchange through the polystyrene is generally ineffective since the vessel wall thickness greatly decreases the permeability rate. Further still, flasks have been made having a cell growth surface that is itself an extremely thin (approximately 0.004 inches thick) flexible, gas permeable membrane. While this type of construction allows for gas exchange, the flexibility and thinness of the growth surface makes the growth of a uniform surface difficult and contributes to problems associated with the durability of the flask.

Gas exchange, particularly the utilization of oxygen by the cells, is a factor that limits the area for cell growth within a cell culture flask. Since flasks for cell culture typically grow attachment dependent cells in a monolayer roughly equal in size to the footprint of the flask, media volume is therefore restricted to an area within the flask permissive to the diffusion of oxygen. Oxygen and carbon dioxide are of particular importance to the culturing of cells. The supply of oxygen for cellular respiration and metabolic function in conventional cell culture containers occupies the head space of the container, e.g., the void space in the container that is above the surface of the cell culture medium. Thus, the volume of the container and the surfaces within conventional cell culture containers are inefficiently used. This results in limiting the rate of gas exchange and/or restricting the equilibration of gases. There is a need for a cell culture flask that can provide an increased surface area for cell growth while still permitting sufficient gas exchange for the multitude of attachment dependent cells.

Desirably, many flasks are stacked together in the incubator and a number of cultures are simultaneously grown. Small variations in the growth medium, temperature, and cell variability have a pronounced effect on the progress of the cultures. Consequently, repeated microscopic visual inspections are needed to monitor the growth of the cells. As such, cell culture flasks are typically constructed of optically clear material that will allow such visual inspection.

With the advent of cell-based high throughput applications, fully automated cell culture systems have been the subject of serious development work (see e.g. A Review of Cell Culture Automation, M. E. Kempner, R. A. Felder, JALA Volume 7, No. 2, April/May 2002, pp. 56-62.) These automated systems employ traditional cell culture vessels (i.e. common flasks, roller bottles, and cell culture dishes) and invariably require articulated arms to uncap flasks and manipulate them much like the manual operator.

There is a need for a cell culture apparatus having a rigid structure that is capable of providing an increased surface area for cell growth while also providing necessary gas exchange. Even further, it is desirable to produce a greater cell yield within commonly known flask volumes while permitting gas exchange at a surface of cell attachment.

Additionally, the desired cell culture apparatus will be suitable for use in the performance of high throughput assay applications that commonly employ robotic manipulation.

SUMMARY OF THE INVENTION

According to an illustrative embodiment of the present invention, a cell growth apparatus for efficient culturing of cells is disclosed. The illustrative apparatus includes a unitary body including a bottom tray defining a cell growth area and a top plate, connected by side walls and end walls. At least one aperture located along any periphery of the apparatus permits access to the internal volume. At least one gas permeable substrate/membrane is affixed to a support internal to the body of the apparatus. A tracheal space/chamber permits gases from an external atmosphere to be exchanged across the gas permeable, liquid impermeable membrane, into and out of the cell culture chamber(s). Further, the tracheal space is an air chamber confined by an outer vessel body. Communication between a tracheal chamber and a cell growth chamber provides a uniformity of conditions for cellular growth. Furthermore, a uniform gaseous distribution can be beneficial in providing consistency in the culturing environment.

One embodiment of a cell growth apparatus of the present invention includes a plurality of cell growth chambers, each having a gas permeable, liquid impermeable surface and an opposing surface. At least one tracheal chamber is in communication with at least one gas permeable, liquid impermeable surface of a cell growth chamber so that cells can exchange gases (e.g. oxygen, carbon dioxide, etc.) with an external environment. The cell growth apparatus of the present invention has at least one tracheal chamber incorporated with a plurality of cell growth chambers combined into one integral unit. The integral unit thus has multiple growth surfaces in any assembled arrangement. A preferred embodiment of a cell growth apparatus of the present invention alternates each cell growth chamber with a tracheal chamber in a vertical successive orientation whereby each cell growth chamber includes a substantially planar horizontal surface supporting the growth of attachment-dependent cells. The cell growth surface, however, may be planar and/or nonplanar to accommodate the surface area for growth. A modified or enhanced surface area in combination with one or more tracheal spaces enables a diversified area for growing cells. Subsequently, another embodiment of the present invention may include an arrangement of surfaces intermediary to cell growth surfaces and tracheal spaces. As such, cell growth chambers may be adjoined and configured so that they still have communication with a tracheal chamber.

When a plurality of cell culture chambers are arranged with tracheal chambers formed there-between, the tracheal chambers permit gaseous exchange between the gas permeable, liquid impermeable surface of a cell culture chamber and the external atmosphere. In a preferred embodiment of the present invention, each cell culture chamber alternates with a tracheal chamber allowing the cells greater access to external gaseous exchange.

One embodiment of the apparatus of the present invention utilizes a gas permeable, liquid impermeable membrane as the opposing surface of a cell culture chamber. In such an embodiment, a plurality of gas permeable substrates (internal to the body of the apparatus) can be incorporated to increase surface area for cellular growth. Preferably then, the apparatus is capable of being rotated to facilitate the growth of attachment-dependent cells on an alternate surface. Each gas permeable substrate may have a tracheal space above and/or below it. One such embodiment is capable of incorporating one or more tracheal spaces between each stacked gas permeable substrate/layer. Additionally, the gas permeable membrane(s) may be treated or coated to promote cell growth.

Another embodiment of the present invention includes one or more supports to form a shelf internal to the apparatus. As such, each shelf would have at least one gas permeable substrate affixed. An alternative embodiment may incorporate lateral ribs traversing the flask body such that an internal gas permeable membrane would be further capable of supporting cellular growth. When such supports or lateral ribs are utilized, a plurality of gas permeable membranes can be arranged or housed within the support itself or affixed to one or more surfaces of the supports. It would therefore be important then, when stacking the layers or gas permeable substrates, to include a tracheal space between each layer of cell growth. Preferably, the tracheal space(s) provide uniform gaseous distribution within the cell culture chamber of the internal apparatus. Completely filling the apparatus with media would allow for optimal cellular nutrient exchange. Consequently, the uniformity of conditions for cellular growth may include a determined media volume per unit surface area. In another aspect, an integral unit of the cell culture apparatus comprises a plurality of modules, each having a cell growth chamber and a tracheal chamber. The plurality of modular gas permeable substrates are utilized to permit a plurality of cell chambers and tracheal chambers to be arranged to form one unitary apparatus of the present invention. The plurality of layers of gas permeable substrates are further capable of being interconnected or adjoined to provide a multiplicity of areas for cellular growth. The plurality of modules may be interconnected in series or staggered to permit continuous flow. For easy assembly and disassembly, individual units having snap-like features could be securely and easily adjoined.

In another embodiment of the present invention, the apparatus comprises a manifold to access the cell growth chambers of an integral unit. The manifold may further be capable of directing the flow of air, liquid, media and/or cellular material within the cell culture chamber.

While many embodiments of the present invention are suitable for static cultures, another embodiment of the present invention staggers the gas permeable substrates within the flask to permit continuous flow through the cell culture chamber. The staggered layers allow media to continuously flow or perfuse through the apparatus.

One embodiment of the present invention provides compliance with conventionally sized and shaped containers currently used such that the apparatus, device or flask of the present invention may be utilized with various equipment and instrumentation. Thus, the apparatus of the present invention may have a substantially rectangular footprint and a substantially uniform height. The rectangular footprint would have dimensions that are substantially identical to an industry standard footprint dimension for microplates. One embodiment of the configuration of the apparatus then may include a neck and/or cap located within the substantially rectangular footprint and that does not exceed the height of the integral unit.

Another embodiment of the apparatus of the present invention may comprise stand-offs either rising from an exterior surface of the top plate or descending from an exterior surface of the bottom tray.

For the addition and removal of media, the cell growth apparatus has at least one access port to access multiple growth chambers. Each cell growth chamber, however, may have individual access ports. Supplementary, the apparatus is capable of being equipped with a septum seal accessible opening or aperture either integrated within the body of the apparatus itself, or as a part of a cap. When a cap is utilized, one embodiment of the apparatus of the present invention, having a height as measured by the distance between an outermost plane of the bottom tray and an outermost plane of the top plate, has a cap, cover, and/or septum covering the aperture. The cap may have a diameter that does not exceed the height of the apparatus/flask so as to prevent interference when the flasks are stacked. Additionally, the cap may be integrally included in a top surface, side, and/or corner region of the apparatus. The apparatus of the present invention may have an aperture which defines an entry portal and another which may define an exit portal. When gas permeable substrates are stacked, the entry and exit portals may be positioned in a parallel or staggered assembly so as to permit flow or perfusion through cell culture chambers within the body of the apparatus.

Convenience then dictates the utilization of one or more optical components, such as microscopic lenses, in communication with individual cell growth chambers. These lenses would allow observation of one or more layers of cell growth. Also, and advantageously so, the apparatus is shaped and configured to enable robotic access to the interior of the apparatus without requiring cumbersome robotic arm manipulation.

The present invention also includes a method of culturing cells in the apparatus of the present invention. The method initially involves providing a apparatus for the growth of cells as previously described. Gas permeable substrates are first assembled into the desired configuration of the apparatus followed by introduction of cells and/or media into the cell culture chamber of the apparatus. Thereafter, the flask can then be incubated to meet the desirable conditions for the growth of cells. Rotation of the apparatus further permits the culturing of cells on an alternate surface of the gas permeable substrate.

BRIEF DESCRIPTION OF THE DRAWINGS

The invention is best understood from the following detailed description when read with the accompanying drawing figures. It is emphasized that the various features are not necessarily drawn to scale. In fact, the dimensions may be arbitrarily increased or decreased for clarity of discussion.

FIG. 1B is a cross-sectional perspective side view of an illustrative embodiment of the present invention.

DETAILED DESCRIPTION

In the following detailed description, for purposes of explanation and not limitation, exemplary embodiments disclosing specific details are set forth in order to provide a thorough understanding of the present invention. However, it will be apparent to one having ordinary skill in the art that the present invention may be practiced in other embodiments that depart from the specific details disclosed herein. In other instances, detailed descriptions of well-known devices and methods may be omitted so as not to obscure the description of the present invention.

Figure 1A:
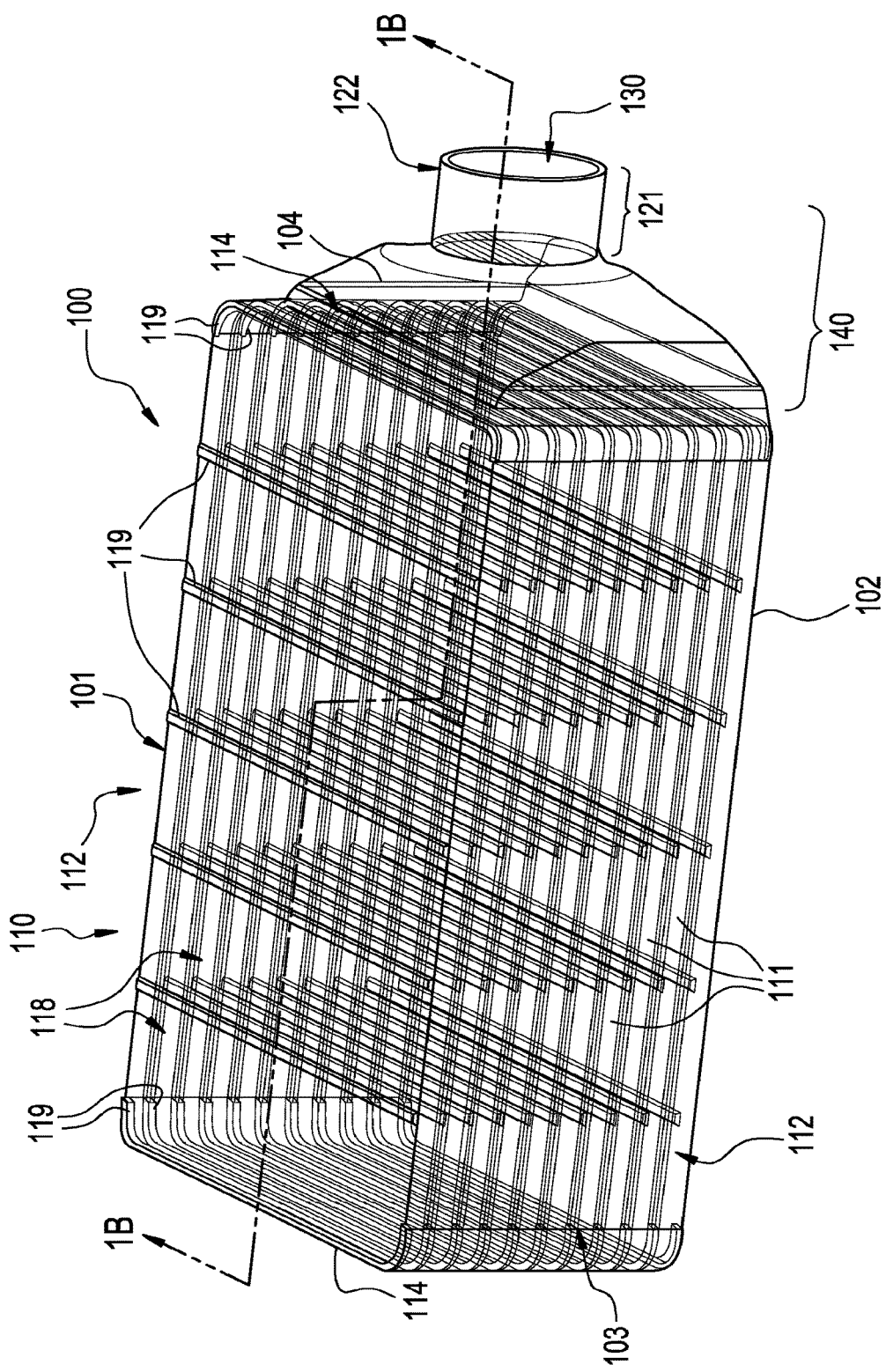
FIG. 1A is a perspective external view of an illustrative embodiment of the apparatus of the present invention.
Figure 1C:
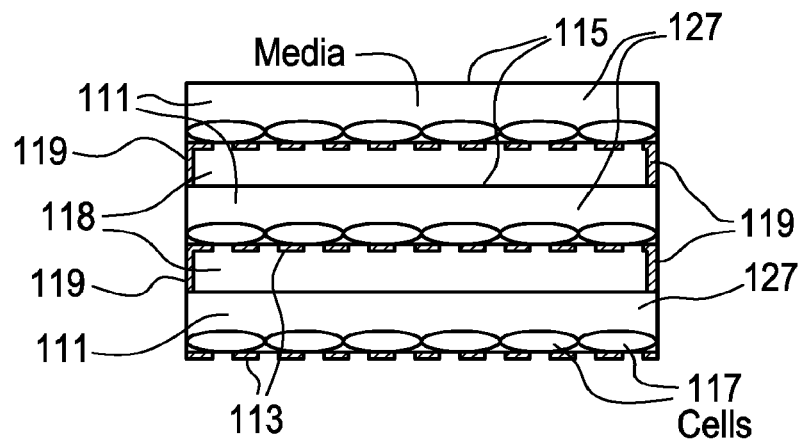
FIG. 1C is a partial internal side view of intermediary supports and gas permeable growth surfaces of FIG. 1A.

An external view of a apparatus in accordance with one embodiment of the present invention is shown in FIG. 1. The apparatus 100 of this embodiment takes the form of a flask 100; the flask 100 comprises an outer vessel body 101 (see FIG. 1A) defined by a top plate 110, a bottom tray 120, sidewalls 112, and end walls 114. Disposed within the flask 100 are individual cell growth chambers 111 as can be seen more clearly in a cross-sectional illustration in FIGS. 1B and 1C. The individual cell growth chambers 111 are each defined by a generally transparent bottom surface 113 and a generally transparent top surface 115. The surfaces 113 and 115 are attached to the flask body 101 along the sidewalls 112 and end walls 114. Preferably, at least one bottom surface 113 within each chamber 111 is gas permeable, liquid impermeable material and capable for the growth of cells 117. Each top surface 115 is preferably a rigid, generally gas impermeable material (preferably transparent) that will provide support to the cell growth chamber 111. In this embodiment, supports 119 allow a gas permeable membrane 113 to be securely adhered thereto in a leak-proof sealing to the flask body 101. Tracheal spaces 118 are created between each cell growth chamber 111. The opposing top surface 115 of the chamber 111 defines an upper wall to the cell growth chamber 111 as well as a bottom portion of a tracheal chamber 118. The tracheal chamber 118 is therefore inclusive of a gas permeable, liquid impermeable surface 113 of a first cell growth chamber and an opposing surface 115 to a second growth chamber 111. Supports 119 further provide structural arrangements to integrally incorporate the surfaces 113 and 115 in forming growth chambers 111 in alternation with tracheal air spaces 118 within the unitary flask 101. Each cell growth chamber 111 therefore alternates with a tracheal chamber 118 in vertical successive orientation. Accessibility to the cellular growth chambers 111 is achieved via an aperture 120 within the flask body 101. The aperture 120 having a necked opening 121 is connected to the cell growth chambers 111 via a manifold 104. The manifold 104 is a portal for manipulation of flask contents. In this embodiment, the necked opening 121 is covered by a cap 122 allowing the flask to be completely filled with media 127 without leakage.

In one embodiment of the present invention, the chambers 111 permit cellular growth on gas permeable membranes 113 such that multiple cell growth chambers 111 are integral with the body 101 of the apparatus 100 and are capable of being completely filled with nutrient media for the growth of cells. The series of tracheal air spaces 118 through the apparatus 100 provide gaseous communication between the cells 117 of the internal volume of the apparatus and the external environment. The tracheal spaces 118 allow oxygenation of media located within cell growth chambers 111 through the gas permeable surfaces 113. Further, the tracheal chambers 118 may take the form of any air gap or space, and do not allow entrance of liquid. As a result, a rigid cell culture apparatus 100 having multiple growth chambers 111, alternating with tracheal spaces 118, is cooperatively constructed to afford the benefit of equivalent gaseous distribution to a large volume of cells 117. Supplementary, the aperture 120 of the flask is resealable by way of a septum and/or cap 122 to prevent contents of the flask from spilling.

The apparatus 100 of the present invention may be made by any number of acceptable manufacturing methods well known to those of skill in the art. In a preferred method, the apparatus 100 is assembled from a collection of separately injection molded parts. Though any polymer suitable for molding and commonly utilized in the manufacture of laboratory ware may be used, polystyrene is preferred. Although not required, for optical clarity, it is advantageous to maintain a thickness of no greater than 2 mm.

Figure 2:
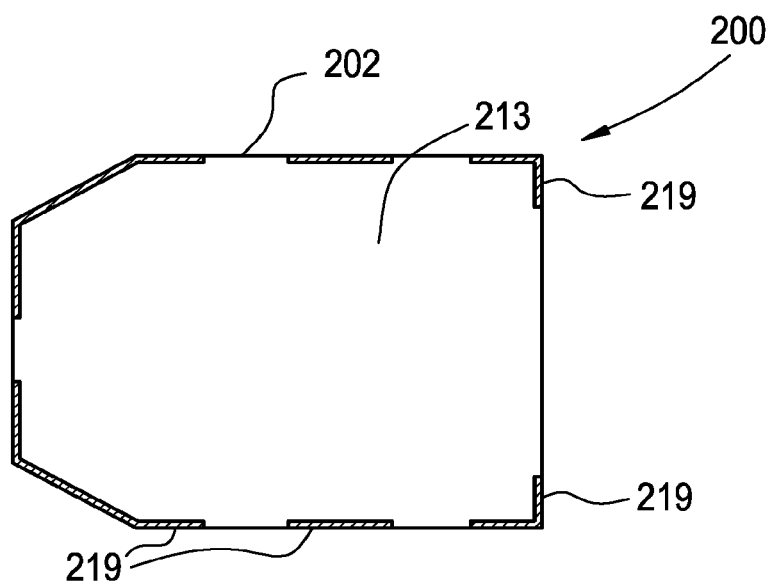
FIG. 2 is a top view of supports utilized in another embodiment of the present invention.
Figure 3:
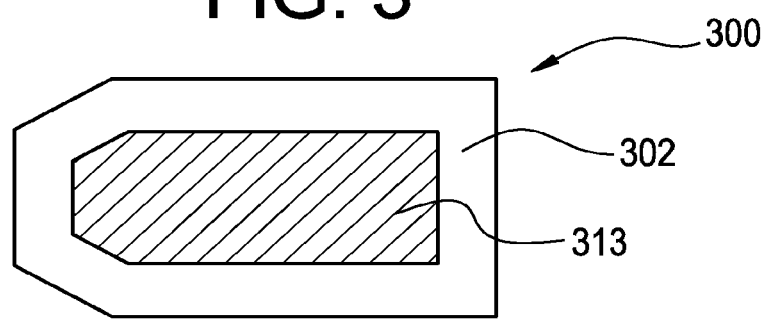
FIG. 3 is an external top view of a frame supporting a gas permeable membrane in another embodiment of the present invention.

The bottom tray 120 and top plate 110 are preferably injection molded. Various sizes and shapes of the supports 119 may be incorporated to facilitate positioning of the membranous layers 113 for cell culture 117 within the internal flask body 101. A top view of another embodiment of the present invention (FIG. 2) has supports 219 as elevated stand-offs 219 along a frame or edge 202 of the flask 100. The supports 219 are rigid structures to support a sheet of gas permeable membrane 213 adhered to the frame 202, as well as provide a structural framework to allow multiple layers (rigid or membranous 213) to be formed within the flask 200. Alternatively, FIG. 3 illustrates an inner surface 313, whereby only a portion of each cell growth chamber 300 is gas permeable. For instance, a rigid frame 302 may support a permeable membrane 313.

Gas permeable, liquid impermeable substrates 113 may be comprised of one or more membranes known in the art. Membranes typically comprise suitable materials that may include for example: polystyrene, polyethylene, polycarbonate, polyolefin, ethylene vinyl acetate, polypropylene, polysulfone, polytetrafluoroethylene (PTFE) or compatible fluoropolymer, a silicone rubber or copolymer, poly(styrene-butadiene-styrene) or combinations of these materials. As manufacturing and compatibility for the growth of cells permits, various polymeric materials may be utilized. For its known competency, then, polystyrene may be a preferred material for the membrane (of about 0.003 inches in thickness, though various thicknesses are also permissive of cell growth). As such, the membrane may be of any thickness, preferably between about 25 and 250 microns, but ideally between approximately 25 and 125 microns. The membrane 113 allows for the free exchange of gases between the interior of the flask and the external environment and may take any size or shape, so long as the membrane is supportive of cellular growth. A preferred embodiment would include a membrane 113 that is additionally durable for manufacture, handling, and manipulation of the apparatus.

The gas permeable membrane 113 is properly affixed to the supports 119 by any number of methods including but not limited to adhesive or solvent bonding, heat sealing or welding, compression, ultrasonic welding, laser welding and/or any other method commonly used for generating seals between parts. Laser welding around the circumference of the membrane 130 is preferred to establish a hermetic seal around the membrane region such that the membrane is flush with and fused to the face of the supports 132 such it becomes an integral portion of the interior surface of the apparatus. Once the gas permeable membrane 130 is adhered, then the top plate 110 and bottom tray 120 may be joined. The parts are held together and are adhesive bonded along the seam, ultrasonically welded, or laser welded. Preferably, laser welding equipment is utilized in a partially or fully automated assembly system. The top plate and tray are properly aligned while a laser weld is made along the outer periphery of the joint.

Advantageously and in order to enhance cell attachment and growth, the surfaces internal to the apparatus 100 are treated to enable cell growth. Treatment may be accomplished by any number of methods known in the art which include plasma discharge, corona discharge, gas plasma discharge, ion bombardment, ionizing radiation, and high intensity UV light.

Finally, when a cap 122 is provided, it may be a screw cap, snap-fit cap, cap with septum, cap with air holes, or any cap known in the art. Preferably, a cap 122 is utilized in which a septum is integral with the cap 122. This will allow a cannula, tip or needle to access the contents of the apparatus 100 without the need for unscrewing. The septum is leak proof, puncturable and capable of resealing once the needle, tip or cannula is removed from the apparatus, even after multiple punctures. In one embodiment, the cap 122 is positioned to access the contents of the apparatus 100 via an end wall 114. As well, the cap 122 may be positioned on a top surface 110. Additionally, the cap arrangement can also be located such that the cap 122 does not protrude from the rectangular footprint as determined by the periphery of the apparatus 100. Other accessibility options may include a neck and cap arrangement within a corner region of the apparatus 100, such that the cap 122 would not protrude from the periphery of the apparatus body 101.

In use, the apparatus 100 of the current invention is employed according to accepted cell growth methods. Cells are introduced to the apparatus 100 though the aperture via the neck (or through a septum in the aperture). Along with the cells 117, media 127 is introduced such that the cells are immersed in the media. The apparatus is arranged such that the cell containing media covers the cell growth surfaces 113. Advantageously, the apparatus 100 is capable of being completely filled with media since the gas permeable membranes 113 in combination with the tracheal spaces 118 provide uniform gas distribution to the cell growth surfaces 113. This will further ensure the flow and exchange of gases between flask interior and the external environment. The apparatus is then placed within an incubator and may be stacked together with similar vessels such that a number of cell cultures are simultaneously grown. The apparatus is situated such that the bottom tray 120 assumes a horizontal position (or vertical position depending on the cell culture application). Another advantage of the apparatus 101 of the present invention is its enhanced capacity to grow cells on an opposing surface 115 when the apparatus is rotated 180°. Thus, when the apparatus is rotated, cells can be cultured on an alternate surface 115. As such, it would be beneficial to have the surface 115 composed of a gas permeable material. Where only gas permeable membranes are layered intermediary to the apparatus, cell growth is therefore enabled on both of its gas permeable surfaces 113/115.

Cell growth is monitored from time to time by microscopic inspection through the generally transparent interior and exterior surfaces of the apparatus 100. Easier accessibility and greater visibility of cellular growth can be visualized when optical lenses having varying magnifications are employed in the external body 101. Additionally, optical lenses may be integrated within other internal surfaces of the apparatus 100.

Additionally, during the cell growth process, it may become necessary to extract the exhausted media and insert fresh media. As previously described, media replacement may be achieved through insertion of a canula, for example, through the septum. Alternatively, the media may be replaced by removing the cap 122, in embodiments that offer this option. Once the cells are ready for harvesting, a chemical additive such as trypsin is added to the apparatus through the septum. The trypsin has the effect of releasing the cells from the surfaces of the apparatus. The cells can then be harvested from the flask.

Figure 4:
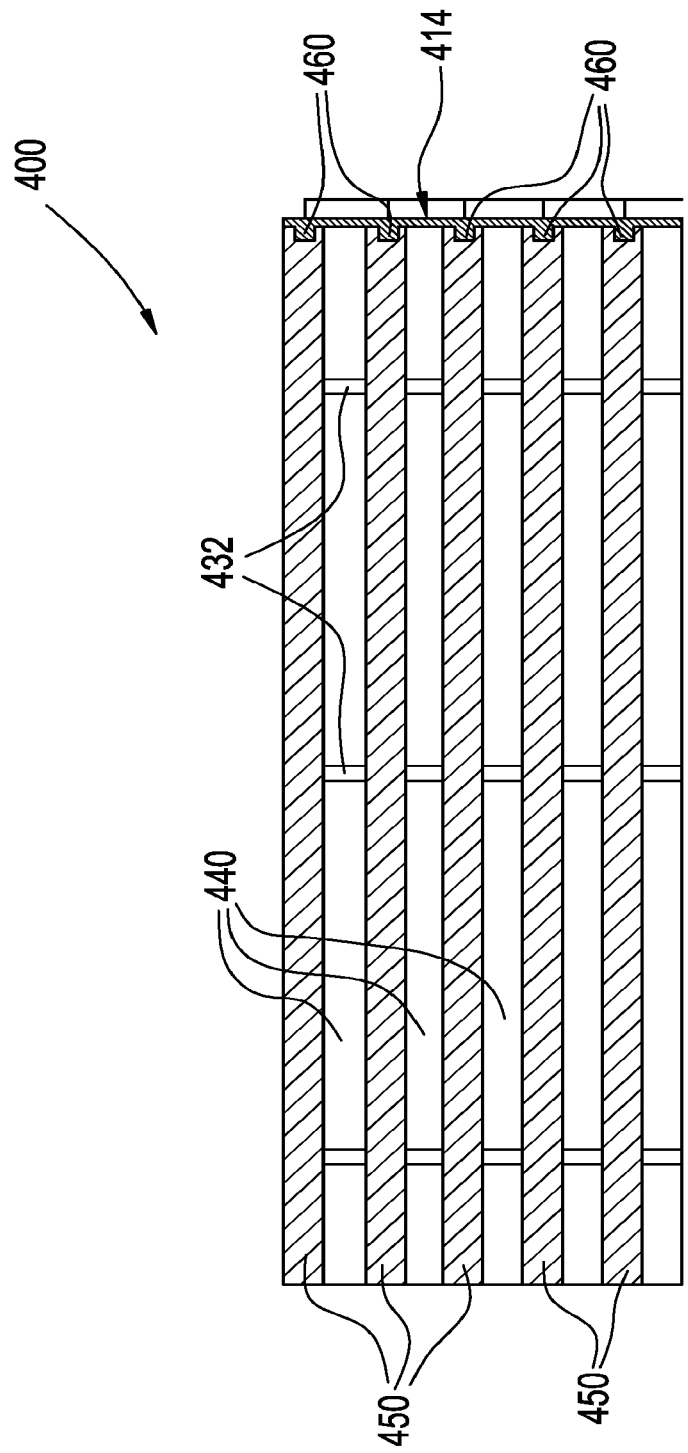
FIG. 4 is a cross-sectional side view of another illustrative embodiment of the present invention.

A cap and neck arrangement is not necessary, however, for an apparatus 400 of the present invention (FIG. 4). As illustrated in this embodiment, supports 432 separate a series of tracheal spaces 440 between each growth layer 450. The tracheal air spaces provide uniform gas distribution within the flask 400 to each cell culture layer 450. In this embodiment, the media in the individual cell growth chambers does not mix as these chambers 450 can be considered separate, and possibly, modular units 450 for easy assembly of the apparatus 400. The chambers 450, however, may be interconnected via hollow supports 432. In one embodiment, access to the interior of the apparatus 400 may be accomplished directly, through plugged ports or apertures 460 that are on an end wall 414 to allow accessibility to each cell culture/media layer 450. Another easy means of access may employ septa as coverings for the apertures 460.

Septa are capable of being integrally affixed to the body of the apparatus 400 by any of the aforementioned methods for affixing a membrane to the wall of the apparatus. The septa may take any form well known to those of skill in the art including a slit arrangement useful for blunt needles and as generally described in WO 02/066595, the contents of which are incorporated herein by reference. Possible materials that may be employed in making the septa include natural and synthetic elastomeric materials including, but not limited to silicone rubber, fluoro-carbon rubber, butyl rubber, polychloroprene rubber, a silicone elastomer composite material, thermoplastic elastomer, medical grades of silicone rubber, polyisoprene, a synthetic isoprene, silicone, santoprene and fluoropolymer laminate and combinations thereof. In a preferred embodiment, the elastomeric material is substantially nontoxic to cultured cells. Moreover, a universal septum may cover each aperture 460 while still allowing access to each individual layer of cell growth 450. This embodiment of the flask 400 may be preferred when stacking of the apparatus 400 is required, or when significant robotic manipulation is encountered since it eliminates the need for cap displacement.

Figure 5:
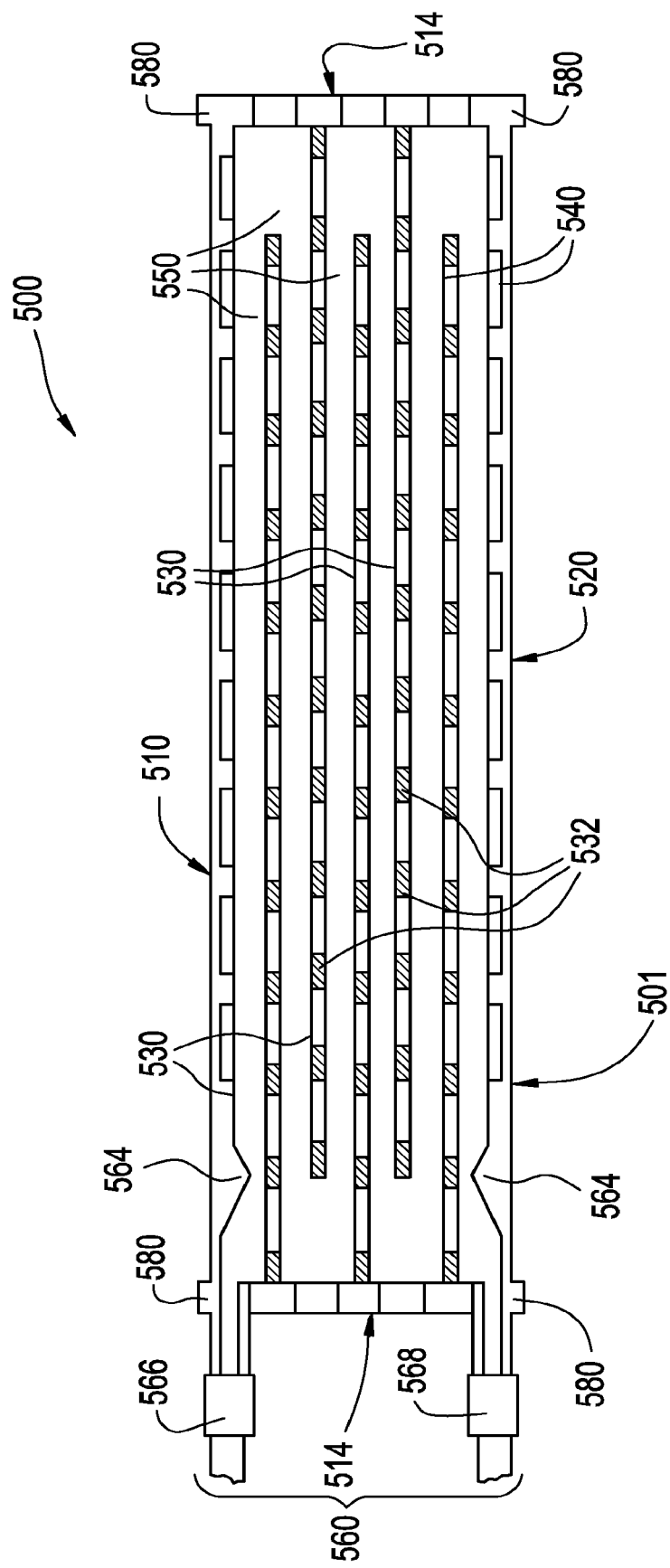
FIG. 5 is an internal side view of the interconnected chambers of one embodiment of the present invention.
Figure 5A:
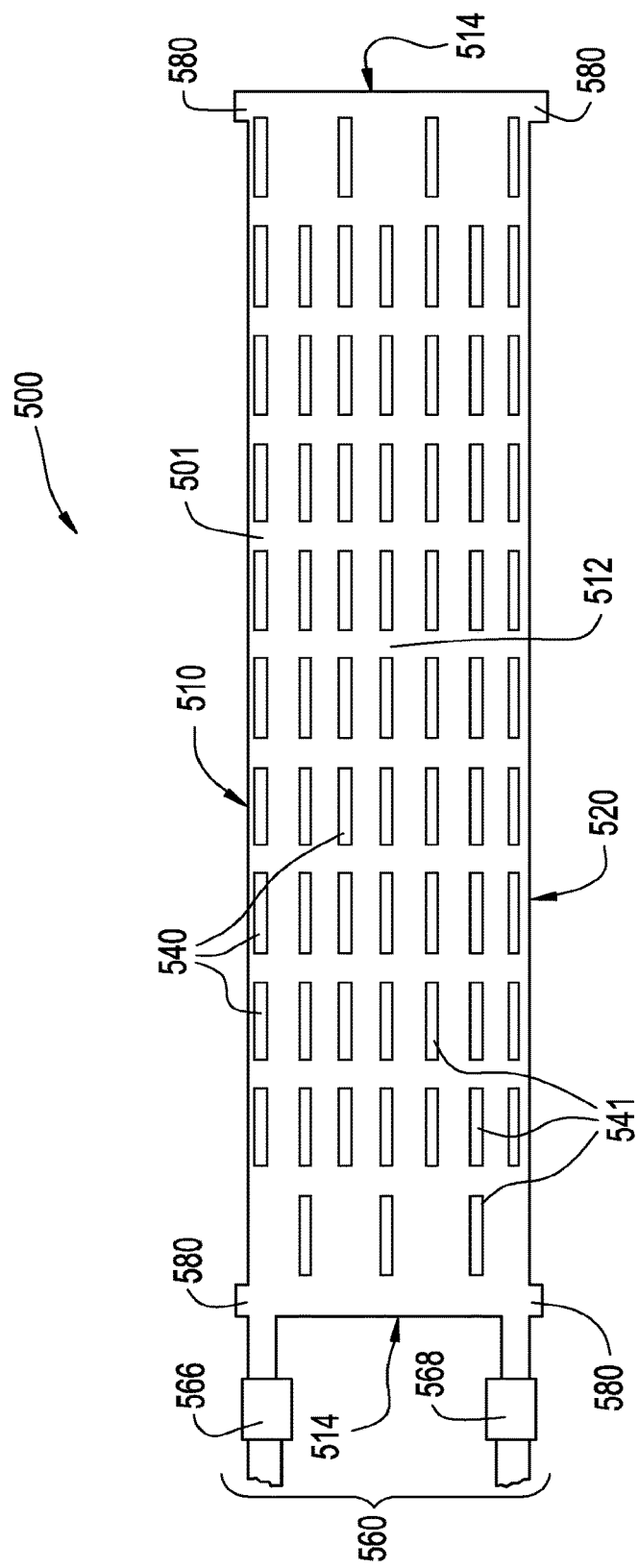
FIG. 5A is a side view of the external frame/body of the embodiment of FIG. 5.

FIGS. 5 and 5A illustrate another embodiment of the present invention. As illustrated in partial internal and external cross-sectional views, respectively, a multilayered culture vessel 501 of the present invention is a perfusion system 500. Multiple gas permeable substrates 530 are adhered to supports/frames 532 and stacked in a parallel configuration permitting an airway or tracheal space 540 to separate each cellular growth layer 550. As in previous embodiments, the gas permeable substrates/membranes 530 in combination with the tracheal chambers 540 define the cell culture system 500. The tracheal spaces 540, alternating with layers of transparent gas permeable membrane(s) 530 and supports 532, provide air/gas exchange with media and cell cultures 550 on an alternate or opposing surface of the gas permeable substrate 530. As such, liquid media inside the apparatus 501 is capable of being contained within a layer 550. In addition, the tracheal air chambers 540 under each cell growth surface 550 have gaseous communication between the cells/media layers 550 and external environment via the series of openings 541 formed between the supports 532 in the external apparatus body 501. The necked opening 560 comprises one aperture which defines an entry portal 562 and one aperture which defines an exit portal 564. The entry portal 566 and exit portal 568 in conjunction with the necked opening 560 allows access to the internal volume/layers 550 of the apparatus 500. Furthermore, in this embodiment of the apparatus/vessel 501, a raised rim 580 serving as a standoff 580 is located on the surfaces of both the top plate 510 and bottom plate 520. The standoff rim 580 is intended to contact the bottom tray 520 of an identical vessel that is stacked on top the apparatus 501. Stacking makes efficient use of incubator space. Another attribute of having a standoff rim 580 is the allowance of an air gap between stacked flasks; the air gap is important for allowing gas exchange through any vent that may be incorporated into an upper or underside surface of the apparatus 501, and further prevents damage to the gas permeable membrane 530. Other alternatives for standoffs 580 include raised corners, posts, ledges, or any other feature that will allow spacing between successively stacked flasks. Preferably, the bottom plate 520 is molded with a rim 580 around the periphery that can engage with a standoff rim 580 from an immediately adjacent apparatus to ensure lateral stability of the stacked vessels.

For exemplary purposes and not limitation, cell seedlings, media exchange, and/or cell harvesting can be accessed via the entry portal(s) 566 and exit portal(s) 568. In combination with the portals 566/568, linear fluid flow restrictors 564 can act as manifolds to evenly direct flow during cell harvesting. Additionally, for exemplary purposes only and not limitation, an embodiment of the present invention incorporates a staggered configuration of gas permeable substrates 530 in conjunction with the supports 532 so as to allow continuous flow or perfusion through the vessel 501. Various arrangements of the layers 550 and stacked substrates 530, however, would permit utilization of the vessel 501 for static cell culture or cell culture in a perfusion system as discussed, including parallel, symmetrical, or asymmetrical arrangements.

Figure 6:
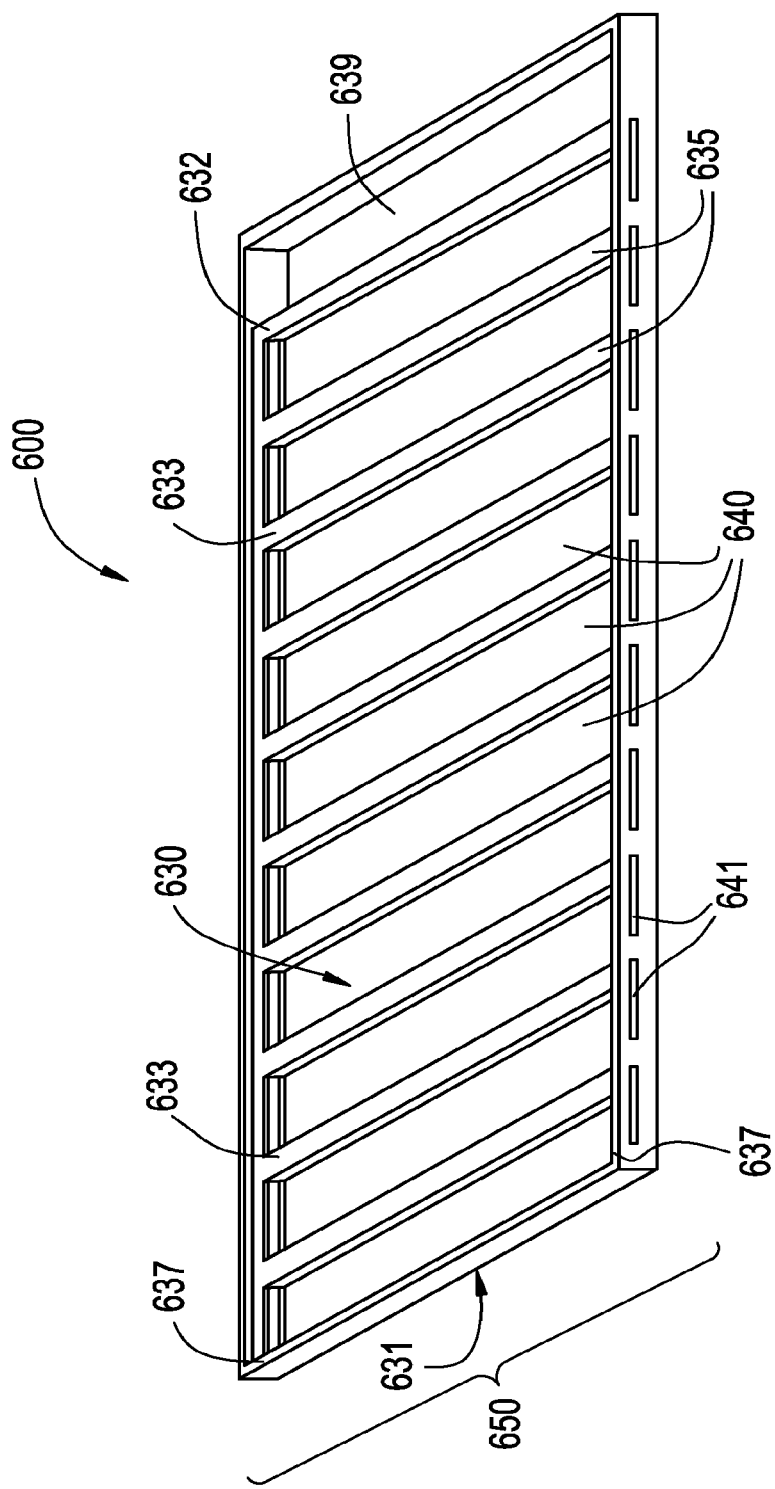
FIG. 6 is an individual unit of one embodiment of the present invention.

For easier accessibility and manufacturing of the multilayered apparatus 501, the arrangement of cell growth layers 550 and stacked substrates 530 into individual modular units 550 may be preferred. As such, a modular unit of one embodiment of the present invention is illustrated in FIG. 6. An individual modular unit 600 comprises a support network 632 in combination with gas permeable membranes/substrates 630. A plurality of modular units 600 are capable of being interconnected and/or interlocked or adhered together to provide a multiplicity of growth surfaces 630/631 that can be easily assembled or disassembled into a unitary multilayered vessel for cellular culture. Vertical stacking of the modular units 600 would be analogous to interconnecting building blocks. Any number of cell growth layers 600 could be assembled or disassembled to provide a wide range of accessibility options to each modular cell growth unit 600. One embodiment of the present invention utilizes supports 632 forming a shelf/frame 633 along a periphery of the individual unit 600 in addition to lateral ribs 635 spanning or bisecting the distance internal to the frame 633. The transparent gas permeable substrate(s) 630 are adhered to supports 632 such that air gaps or tracheal spaces 640 are formed between each cell layer of gas permeable substrate 630 to allow gas distribution throughout the unitary apparatus when multiple trays are assembled into one vessel body. The tracheal spaces 640 have gaseous exchange with the external atmosphere via the tracheal openings/ports 641 in the external frame 633. Further, the tracheal spaces 640 provide air/gas exchange with media and cell cultures on a [primary] surface 630 and an alternate or secondary surface 631, both surfaces 630/631 capable of cell growth. As seen in this embodiment, peripheral ridges or elevations 637 of the support system 632 are utilized to facilitate stacking of the modular units 600. The gas permeable membrane 630, however, may be adhered to any of the surfaces of the support system 632 or peripheral edge 637 so as to provide a leak-proof gas permeable substrate 630 in combination with the modular unit 600 and further permitting multiple areas for cell growth on the gas permeable surfaces 630/631. Additionally, an open end 633 of the frame 632 is a feature to permit fluid flow when multiple modular units 600 are stacked and adhered together into a unitary body so as to be utilized in perfusion devices. Furthermore, one embodiment of the apparatus of the present invention encompasses one gas permeable substrate 630 providing a primary growth surface 630, as well as an [optional] gas permeable substrate 631 providing a secondary growth surface 631 adhered to an underside of the frame network 632.

Figure 7:
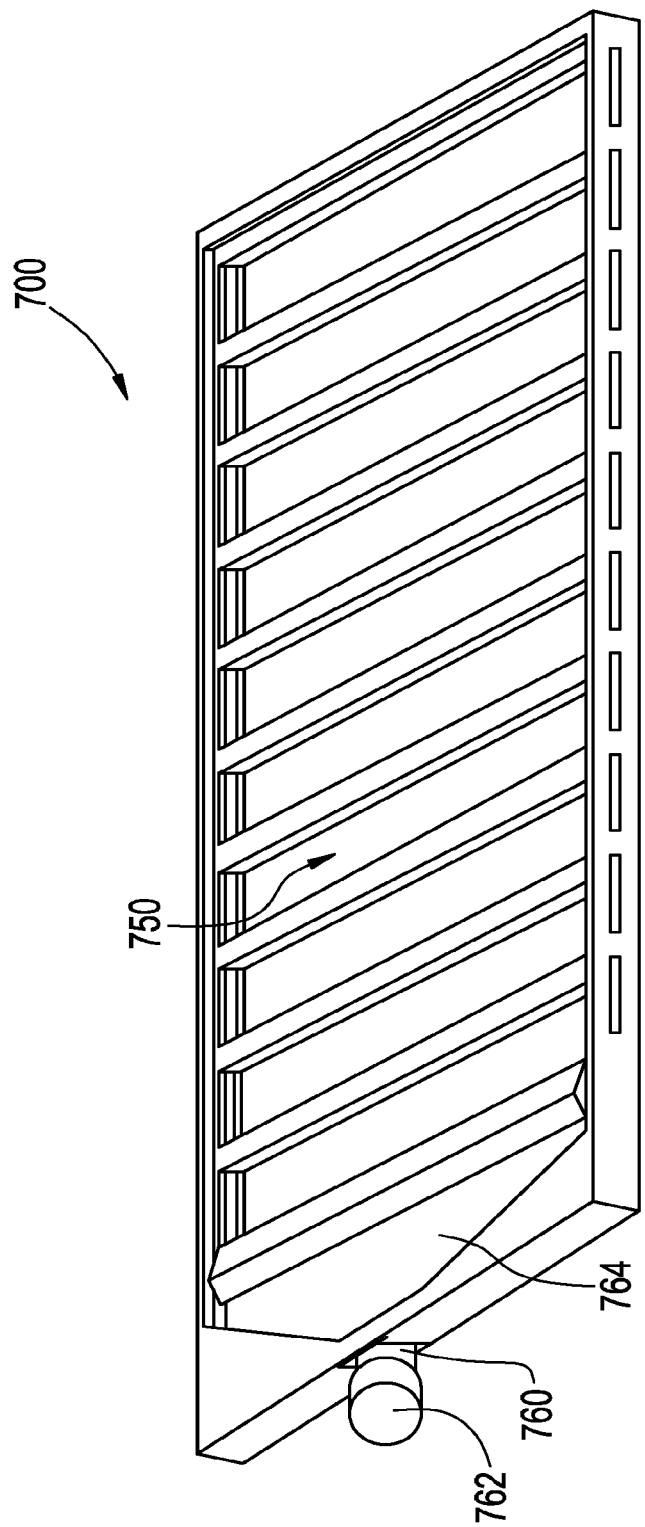
FIG. 7 is another individual unit or tray of an embodiment of the present invention.

As seen in FIG. 7, another embodiment of the present invention utilizes a modular unit 700 inclusive of a cap 762 covering an aperture 760. A manifold 764 permits access to the internal cell culture layer 750. A unitary cell culture chamber is capable of being constructed when individual units 600 and/or 700 are stacked. Further, when combined, the internal cell culture layers 650 and/or 750 would be accessible via the aperture 760 to the unitary cell culture chamber.

In utilizing the vessels of the current invention, various methods in the industry may be employed in accordance with accepted cell growth culturing. As discussed in a previous embodiment, cells are introduced to the flask though the neck or through the septum. Along with the cells, media is introduced such that the cells are immersed in the media. The apparatus is arranged such that the cell-containing media covers the cell growth surfaces. Advantageously, the apparatus is capable of being completely filled with media since the gas permeable membranes in combination with the tracheal spaces provide uniform gas distribution to the cell growth surfaces. This will furthermore ensure the flow and exchange of gases between flask interior and the external environment. The apparatus is then placed within an incubator and may be stacked together with similar flasks such that a number of cell cultures are simultaneously grown. The flask is situated such that the bottom tray assumes a horizontal position (or vertical position depending on the cell culture application). The flask can then be rotated to permit the culturing of cells on an alternate surface. Where only gas permeable membranes are layered intermediary to the apparatus, cell growth is enabled on upper and under sides of the membrane (opposing gas permeable surfaces).

Cell growth can be monitored from time to time by microscopic inspection through the generally transparent surfaces. If more detailed visual inspection of the cell growth layers is required, optical lenses can be integrated into the body or frame of the apparatus. As such, varying magnifications of the optical lenses would permit viewing within individual layers without disassembly of the apparatus. Optical lenses may be incorporated into any surface or modular unit, as well, preferably when the units are capable of being disassembled for observational analysis.

During the cell growth process, it may become necessary to extract the exhausted media and insert fresh media. As previously described, media replacement may be achieved through insertion of a canula, for example, through the septum. Alternatively, the media may be replaced by removing the cap, in embodiments that offer this option. Once the cells are ready for harvesting, a chemical additive such as trypsin is added to the flask through the septum. The trypsin has the effect of releasing the cells from the vessel surfaces. The cells are then harvested from the apparatus.

As discussed, the embodiments of the present invention are for exemplary purposes only and not limitation. Supplementary, tracheal spaces are capable of being formed above and/or below the support network when the trays are stacked upon one another where peripheral ridges of individual modular units permit gaps of air to flow through gas permeable substrates to cell growth areas when the units are interconnected. The tracheal spaces formed within the individual units are further capable of including a diversified network of supports, intersecting and/or alternating gas permeable membrane with supports and air/tracheal spaces.

Figure 8:
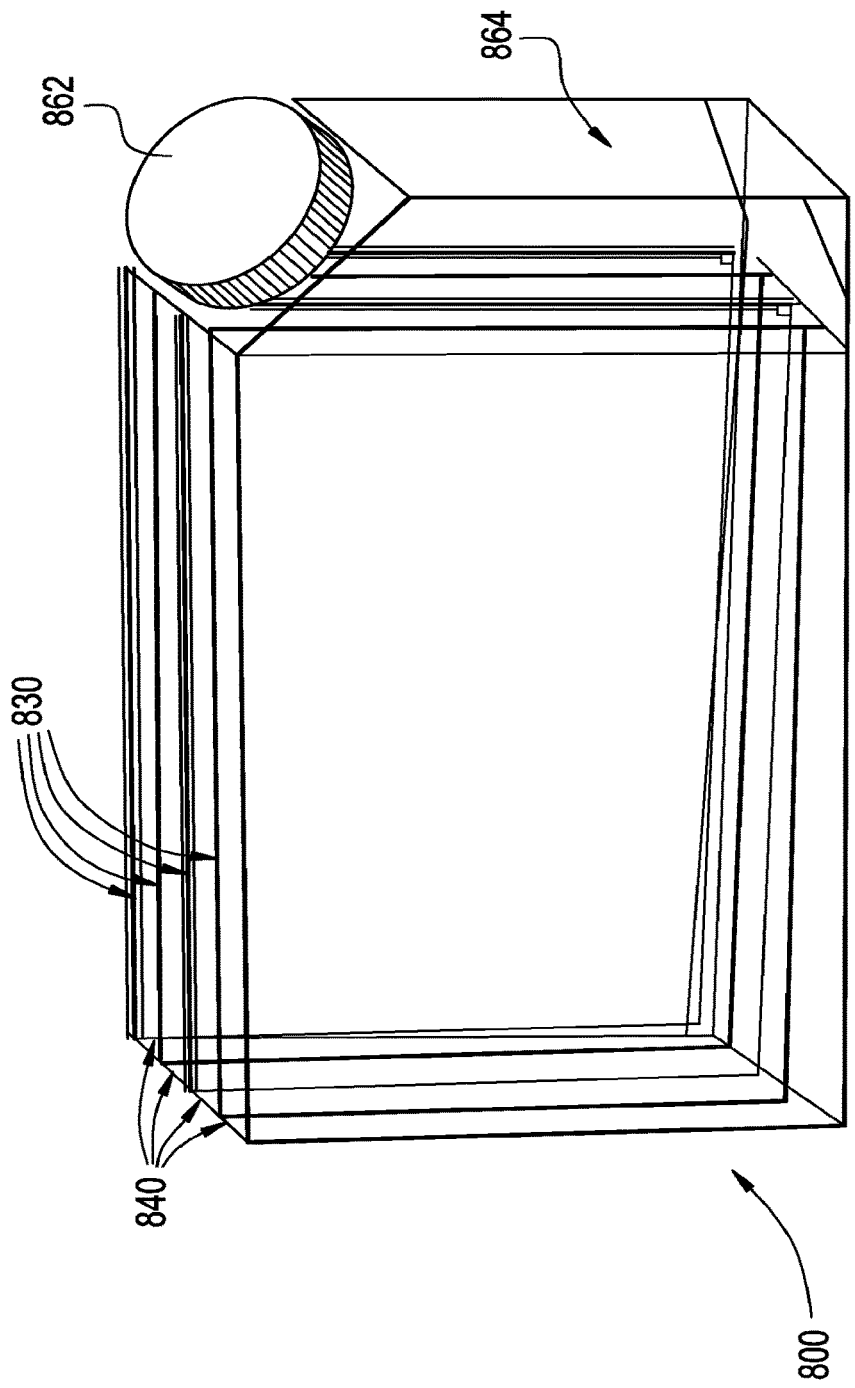
FIG. 8 is an alternative embodiment of the present invention.

The gas permeable substrates utilized in the embodiments of the present invention are capable of cell growth and gas exchange with the external environment, achieving uniform gaseous distribution throughout the cell culture vessel. Furthermore, the apparatus of the present invention may utilize horizontal or vertical designs having surfaces arranged for uniform gaseous distribution to cell growth areas. As seen in one embodiment of the present invention in FIG. 8, vertical growth surfaces or gas permeable substrates 830 are separated by tracheal spaces 840. The tracheal spaces 840 allow for the exchange of oxygen, carbon dioxide, and other various gases between the respiratory/gas permeable surfaces 830 that the cells grow on and the incubator or external atmosphere where the apparatus 800 is stored while the cells are given time to grow. The apparatus 800 of the present invention may include a cap 862 and/or a manifold 864, as well, which is unitary with the vessel body 800.

Figure 9:
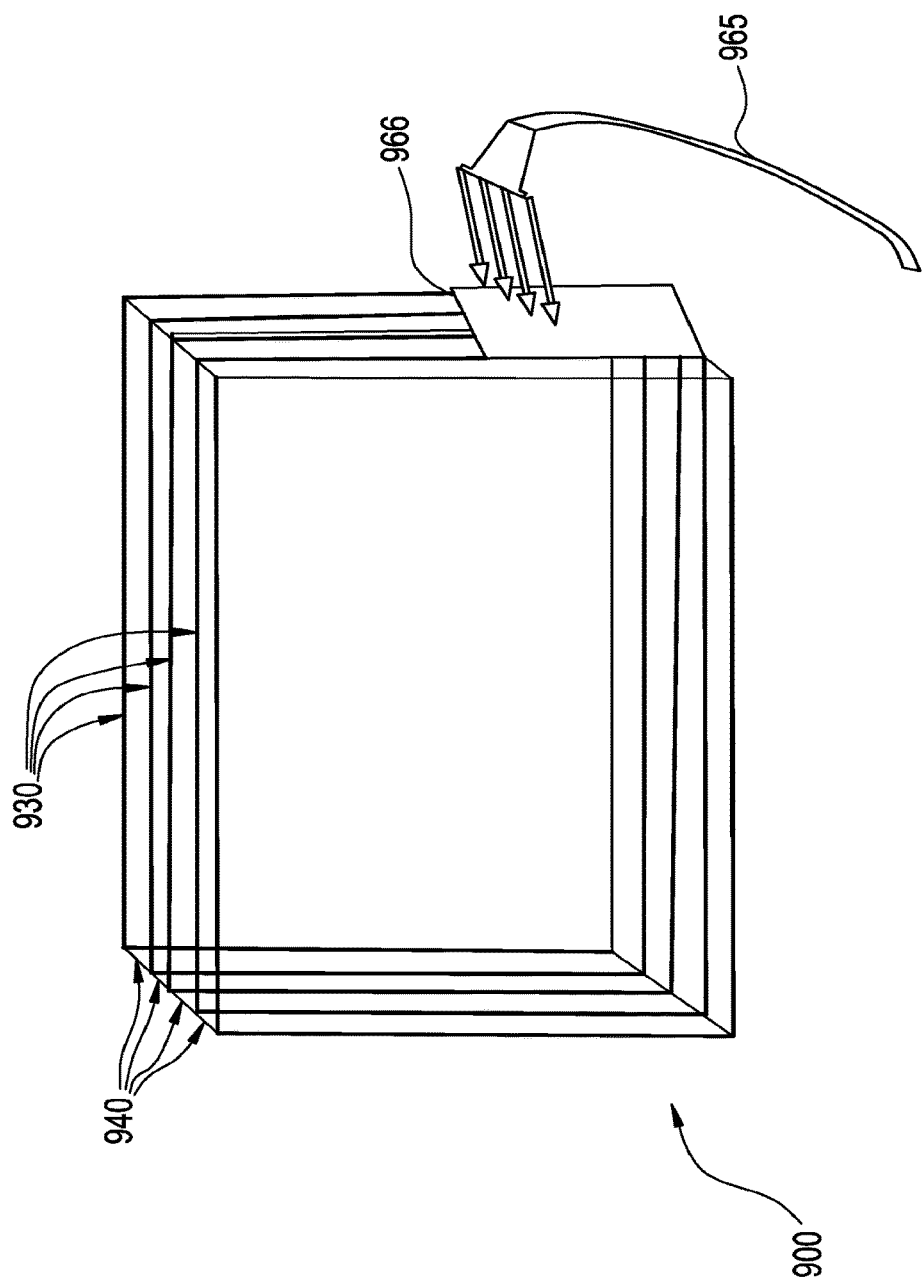
FIG. 9 is another embodiment of the present invention.

Another embodiment of the present invention (FIG. 9) is an apparatus 900 that includes an external manifold 965 allowing access to individual cell growth layers 930 via a septum as discussed previously. The units 930 are modular and joined together to handle as one. Furthermore, tracheal spaces 940 allow uniform gaseous distribution to cell growth areas 930 throughout the flask 900. The uniformity of conditions for cellular growth may include a determined media volume per unit surface area. Though the determined ratio of volume per unit surface area has previously been known within a confined range of about 0.5-1.0 ml/cm$^2$, the ratio is no longer limiting due to the direct access of the cells to gaseous exchange via the gas permeable membrane upon which the cells grow. While efficient use of media is still preferable, any volume of media may be utilized in an apparatus of this invention, the apparatus of which may be any size and/or take any shape. Further, the enhanced capabilities of the present invention may incorporate tracheal spaces in combination with cell growth chambers into standardized or conventionally-sized containers. One embodiment of the apparatus of the present invention includes an increased surface area for cellular growth preferably with a ratio of media volume per unit surface area in the range of about 0.25-0.50 ml/cm$^2$; however, the dimensions and confines for cellular growth are unlimited. One such embodiment would include a height of about 2.8 mm. As stated previously, however, the height is unrestricted so long as it permits area for the growth of cells. Furthermore, by completely filling the cell growth chambers with media, the cells have access to optimal nutrient exchange.

The embodiments of the present invention may be modified to take the shape of any device, container, apparatus, vessel, or flask currently used in industry. Specifically, cylindrical or alternative vessels may utilize gas permeable substrates (internal to the vessel) in combination with tracheal chambers or spaces to provide an improved culturing environment for the growth of cells. A spiral or alternative approach inclusive of a tracheal chamber would therefore be possible. Further, although tracheal chambers may take many forms and be of any size, the passageway-like chambers are: a) confined air spaces, b) in communication with a gas permeable membrane that is permissive to cell growth, and c) communicative with the external environment via open direct access and/or additional gas permeable membranes.

As presented, the multiple embodiments of the present invention offer several improvements over standard vessels currently used in industry. The improved cell culture devices remarkably enhance the volume of cells that are capable of being cultured in the volume enclosed by traditional cell culture vessels. The various benefits are attributable to the multi-layered arrangement of gas permeable membranes assembled into a unitary vessel. Successive layering of individual growth chambers and tracheal chambers inclusive of the gas permeable membranes makes oxygen and other gases from the external environment available to the internal contents of the apparatus. Specifically, gaseous exchange with the nutrient media is conducive to an even distribution of cell growth when gas permeable membranes are utilized on at least one potential growth surface. The cell growth apparatus is capable of fully utilizing its capacity by allowing cells access to optimal volumes of nutrient media and direct oxygenation via the tracheal spaces. Additional benefits are afforded to the cell culturing apparatus in which the exterior framework is rigidly constructed, conveniently offering easy handling, storage, and accessibility.

In one embodiment, the present invention has a footprint conforming to industry standard for microplates (5.030+/−0.010 inches by 3.365+/−0.010 inches). For this reason, the neck portion is preferably recessed within the overall rectangular footprint. The advantage of providing an apparatus with such a footprint is that automated equipment designed specifically for the manipulation of microplates may be utilized with this apparatus with very little customized modification. Similarly the height, or the distance between the outer most portion of the bottom tray and the outer portion of the top plate, is approximately 0.685+/−0.010 inches. At any rate, the present invention is not intended to be limited in any way by the aforementioned preferred dimensions and in fact may be constructed to any dimension.

As exemplified, the apparatus may include any unitary structure, vessel, device or flask with the capacity to integrally incorporate substrates in successive orientation. The invention being thus described, it would be obvious that the same may be varied in many ways by one of ordinary skill in the art having had the benefit of the present disclosure. Such variations are not regarded as a departure from the spirit and scope of the invention, and such modifications as would be obvious to one skilled in the art are intended to be included within the scope of the following claims and their legal equivalents.

The invention claimed is:

1. A cell culture vessel comprising:
a top plate;
a bottom tray opposed to the top plate;
a manifold; and
a plurality of vertically spaced and aligned cell growth chambers that are between the top plate and the bottom tray, each cell growth chamber defined by a gas permeable, liquid impermeable membrane bottom surface, and a top surface, said top and bottom surfaces attached to a pair of side walls and end walls, wherein the top surface of a first cell growth chamber and the gas permeable, liquid impermeable membrane bottom surface of a second cell growth chamber adjacent the first cell growth chamber define a tracheal space, said tracheal space being in gaseous communication with the external environment through a plurality of openings, each opening defined by supports extending vertically between the side walls and end walls of adjacent cell growth chambers, and wherein one of the end walls comprises an opening that allows fluid communication between the cell growth chambers and the manifold.

2. The cell culture vessel of claim 1, wherein the manifold comprises an aperture with a necked opening.

3. The cell culture vessel of claim 2, wherein the aperture is covered by a cap.

4. The cell culture vessel of claim 1 further comprising:
one or more internal supports extending from the top surface of a first cell growth chamber and supporting the gas permeable, liquid impermeable membrane bottom surface of a second cell growth chamber adjacent the first cell growth chamber.

5. The cell culture vessel of claim 1, wherein each of the cell growth chambers are less than 3 mm in height.

6. The cell culture vessel of claim 1, wherein the gas permeable, liquid impermeable membrane bottom surface comprises a material selected from the group consisting of polystyrene, polyethylene, polycarbonate, polyolefin, ethylene vinyl acetate, polypropylene, polysulfone, polytetrafluoroethylene (PTFE), a silicone rubber or copolymer, poly (styrene-butadiene-styrene), and any combination thereof.

7. The cell culture vessel of claim 1, wherein the gas permeable, liquid impermeable membrane bottom surface has a thickness of 25-125 microns.

8. The cell culture vessel of claim 1, wherein the top surface of each cell growth chamber comprises a gas permeable, liquid impermeable membrane.

9. The cell culture vessel of claim 8, wherein the gas permeable, liquid impermeable membrane top surface comprises a material selected from the group consisting of polystyrene, polyethylene, polycarbonate, polyolefin, ethylene vinyl acetate, polypropylene, polysulfone, polytetrafluoroethylene (PTFE), a silicone rubber or copolymer, poly (styrene-butadiene-styrene), and any combination thereof.

10. The cell culture vessel of claim 8, wherein the gas permeable, liquid impermeable membrane top surface has a thickness of 25-125 microns.

* * * * *

UNITED STATES PATENT AND TRADEMARK OFFICE
CERTIFICATE OF CORRECTION

| | | |
|---|---|---|
| PATENT NO. | : 11,274,273 B2 | Page 1 of 3 |
| APPLICATION NO. | : 15/671485 | |
| DATED | : March 15, 2022 | |
| INVENTOR(S) | : Gregory Roger Martin et al. | |

It is certified that error appears in the above-identified patent and that said Letters Patent is hereby corrected as shown below:

On the Title Page

On the page 4, in Column 1, Item (56) under "Other Publications", Line 7, delete "Measureing" and insert -- Measuring --.

On the page 4, in Column 2, Item (56) under "Other Publications", Line 17, delete "CellGeniz," and insert -- CellGenix, --.

On the page 5, in Column 1, Item (56) under "Other Publications", Line 43, delete "Dapstick," and insert -- Capstick, --.

On the page 5, in Column 1, Item (56) under "Other Publications", Line 45, delete "Dapstick" and insert -- Capstick --.

On the page 5, in Column 1, Item (56) under "Other Publications", Line 49, delete "Ph D." and insert -- Ph.D. --.

On the page 5, in Column 1, Item (56) under "Other Publications", Line 50, delete "90/014,541" and insert -- 90/014,540 --.

On the page 5, in Column 1, Item (56) under "Other Publications", Line 53, delete "3(4):" and insert -- 8(4): --.

On the page 5, in Column 1, Item (56) under "Other Publications", Line 58, delete "90/014,538," and insert -- 90/014,540, --.

On the page 5, in Column 1, Item (56) under "Other Publications", Line 58, delete "90/014,538," and insert -- 90/014,541, --.

Signed and Sealed this
Thirteenth Day of January, 2026

John A. Squires
*Director of the United States Patent and Trademark Office*

On the page 5, in Column 1, Item (56) under "Other Publications", Line 61, delete "90/014,538," and insert -- 90/014,540, --.

On the page 5, in Column 1, Item (56) under "Other Publications", Line 61, delete "90/014,538," and insert -- 90/014,541, --.

On the page 5, in Column 2, Item (56) under "Other Publications", Line 33, delete "90/014,538." and insert -- 90/014,538]. --.

On the page 5, in Column 2, Item (56) under "Other Publications", Line 44, delete "at" and insert -- et --.

On the page 6, in Column 1, Item (56) under "Other Publications", Line 29, delete "J:20" and insert -- 0:20 --.

On the page 6, in Column 1, Item (56) under "Other Publications", Line 61, delete "90/014,538," and insert -- 11/952,848, --.

On the page 6, in Column 1, Item (56) under "Other Publications", Line 63, delete "90/014,538," and insert -- 11/952,848, --.

On the page 6, in Column 1, Item (56) under "Other Publications", Line 65, delete "90/014,538," and insert -- 11/952,848, --.

On the page 6, in Column 2, Item (56) under "Other Publications", Line 15, delete "90/014,541," and insert -- 10/961,814, --.

On the page 6, in Column 2, Item (56) under "Other Publications", Line 25, delete "3,415,144" and insert -- 8,415,144 --.

On the page 6, in Column 2, Item (56) under "Other Publications", Line 28, delete "3,697,443" and insert -- 8,697,443 --.

On the page 6, in Column 2, Item (56) under "Other Publications", Line 33, delete "3,518,692" and insert -- 8,518,692 --.

On the page 6, in Column 2, Item (56) under "Other Publications", Line 36, delete "3,168,432" and insert -- 8,168,432 --.

On the page 6, in Column 2, Item (56) under "Other Publications", Line 39, delete "3,158,426" and insert -- 8,158,426 --.

CERTIFICATE OF CORRECTION (continued)
U.S. Pat. No. 11,274,273 B2

On the page 6, in Column 2, Item (56) under "Other Publications", Line 42, delete "3,158,427" and insert -- 8,158,427 --.

On the page 6, in Column 2, Item (56) under "Other Publications", Line 65, delete "D:20" and insert -- 0:20 --.

On the page 7, in Column 1, Item (56) under "Other Publications", Line 1, delete ":<https://ecatalog.coming.com/" and insert -- :<https://ecatalog.corning.com/ --.

On the page 7, in Column 2, Item (56) under "Other Publications", Line 8, delete "(D1135)," and insert -- (DI 135), --.

On the page 7, in Column 2, Item (56) under "Other Publications", Line 8, delete "Coming" and insert -- Corning --.

On the page 7, in Column 2, Item (56) under "Other Publications", Line 11, delete "(D1137)," and insert -- (DI 137), --.

On the page 7, in Column 2, Item (56) under "Other Publications", Line 20, delete "Coming" and insert -- Corning --.